US006998252B1

(12) United States Patent
Moss et al.

(10) Patent No.: US 6,998,252 B1
(45) Date of Patent: *Feb. 14, 2006

(54) RECOMBINANT POXVIRUSES HAVING FOREIGN DNA EXPRESSED UNDER THE CONTROL OF POXVIRUS REGULATORY SEQUENCES

(75) Inventors: Bernard Moss, Bethesda, MD (US); Michael Mackett, Manchester (GB); Geoffrey L. Smith, Oxford (GB)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/470,360

(22) Filed: Jun. 6, 1995

Related U.S. Application Data

(63) Continuation of application No. 07/987,546, filed on Dec. 7, 1992, which is a continuation of application No. 07/539,169, filed on Jun. 18, 1990, now abandoned, which is a continuation of application No. 07/072,455, filed on Jul. 13, 1987, now abandoned, which is a continuation-in-part of application No. 06/555,811, filed on Nov. 28, 1983, now abandoned, and a continuation-in-part of application No. 06/445,892, filed on Dec. 1, 1982, now abandoned, and a continuation-in-part of application No. 06/445,451, filed on Nov. 30, 1982, now abandoned.

(51) Int. Cl.
*C12N 15/863* (2006.01)
*C12N 7/01* (2006.01)
*C12N 15/64* (2006.01)
*C12N 15/09* (2006.01)

(52) U.S. Cl. .............. 435/69.1; 435/320.1; 435/235.1; 435/91.4; 435/91.41; 435/69.3

(58) Field of Classification Search ............. 435/172.3, 435/235.1, 69.1, 69.3, 320.1, 91.4, 91.41; 935/32, 34, 36, 57, 65
See application file for complete search history.

(56) References Cited

U.S. PATENT DOCUMENTS

| | | | |
|---|---|---|---|
| 4,603,112 A | | 7/1986 | Paoletti et al. |
| 4,722,848 A | | 2/1988 | Paoletti et al. |
| 4,769,330 A | * | 9/1988 | Paoletti et al. ........... 435/172.3 |
| 5,110,587 A | | 5/1992 | Paoletti et al. |
| 5,155,020 A | | 10/1992 | Paoletti |
| 5,174,993 A | * | 12/1992 | Paoletti .................... 424/199.1 |
| 5,204,243 A | | 4/1993 | Paoletti |
| 5,225,336 A | | 7/1993 | Paoletti |
| 5,266,313 A | * | 11/1993 | Esposito et al. ......... 424/199.1 |
| 5,338,683 A | | 8/1994 | Paoletti |
| 5,364,773 A | | 11/1994 | Paoletti et al. |
| 5,494,807 A | | 2/1996 | Paoletti et al. |
| 5,505,941 A | | 4/1996 | Paoletti |
| 5,583,028 A | | 12/1996 | Paoletti et al. |

FOREIGN PATENT DOCUMENTS

| | | | |
|---|---|---|---|
| EP | 0083286 | | 7/1983 |
| EP | 0284416 | | 9/1988 |
| EP | 0338807 | | 10/1989 |
| EP | 0397560 | * | 11/1990 |
| EP | 0397560 A2 | | 11/1990 |
| WO | WO-89/03429 | * | 4/1989 |
| WO | WO 89/03429 A1 | | 4/1989 |
| WO | WO 89/12684 | | 12/1989 |
| WO | WO89/12684 | | 12/1989 |
| WO | WO-93/25666 | * | 12/1993 |
| WO | WO 93/25666 A1 | | 12/1993 |

OTHER PUBLICATIONS

Boyle and Coupar, J. Gen. Virol. 67: 1591-1600.*
Boyle et al, Virology 156: 355-365.*
Muller et al, J. Gen. Virol. 38:135-147.*
Prideaux et al, Arch. Virol. 96:185-199.*
Schnitzlein et al, Virus Research 10:65-75.*
Arif, Advances in Virus Research 29:195-213.*
Langridge, Journal of Invertebrate Pathology 42: 369-375.*
Massung et al. Virology 180:355-364.*
Foley et al, Annals of the New York Academy of Science, 646:220-222.*
Joklik et al, 17th edition Zinser Microbiology, 1Apple-Centurion-Crofts, New York, p. 1009.*
Pickup DJ et al. Proceedings of the National Academy of Sciences USA 79: 7112-6.*
McFadden et al (Cell 18:101-8, Sep. 1979).*
Moss et al (Journal of Virology 40:387-95, Nov. 1981).*
Nakano et al (PNAS 79: 1593-1596, Mar. 1, 1982.*
Panicali et al (PNAS 79:4927-4931, Aug. 1982).*
Weir et al (PNAS 79(4): 1210-1214, Feb. 15, 1982).*
Moyer et al (Virology 102:119-132, 1980).*
Mackett et al (PNAS 79:7415-7419, Dec. 1, 1982).*
Esposito et al (Virology 165:313-6, Jul. 1988).*

(Continued)

*Primary Examiner*—Mary E. Mosher
(74) *Attorney, Agent, or Firm*—Heller Ehrman LLP

(57) ABSTRACT

Recombinant poxviruses, such as vaccinia, are provided that comprises a segment comprised of (A) a first DNA sequence encoding a polypeptide that is foreign to poxvirus and (B) a poxvirus transcriptional regulatory sequence, wherein (i) said transcriptional regulatory sequence is adjacent to and exerts transcriptional control over said first DNA sequence and (ii) said segment is positioned within a nonessential genomic region of said recombinant poxvirus. Vaccines, carriers, cells, and media comprising recombinant poxviruses, and methods of immunization with recombinant poxviruses also are provided.

14 Claims, 3 Drawing Sheets

OTHER PUBLICATIONS

Boyle et al (Virus Research 10:343-356, 1988).*
Taylor et al (Vaccine 6:497-503, Dec. 1988).*
Taylor et al (Vaccine 6:504-508, Dec. 1988).*
Venkatesan et al (Cell 125:805-814, 1981).*
Weir et al (Journal of Virology 46(2): 530-7, May 1983).*
Weir et al (Journal of virology 51(3):662-669, 1984).*
Bertholet et al (PNAS 82(7): 2096-2100, Apr. 1985).*
Boyle et al (Journal of General Virology 67:1591-1600, 1986).*
Panicali et al (PNAS 80(17): 5364-5368, Sep. 1, 1983).*
Smith et al, Nature 302 (5908): 490-5,Apr. 7, 1983.*
Smith et al, PNAS 80:23, 7155-7159, Dec. 1, 1983.*
Webster's New World Dictionary of the American Language. College Edition. 1968. The World Publishing Company, Cleveland and New York. p. 18.*
Baldick et al., *J. Virol.* 66: 4710-4719 (1992).
Belle et al., *Virology* 112: 306-317 (1981).
Bertholet et al., *Proc. Nat'l. Acad. Sci. USA* 82: 2096-2100 (1985).
Boone et al., *Virology* 79: 67-80 (1977).
Fenner et al., *Virology* 11: 185 (1960).
Green et al., *Cell* 22: 231-242 (1980).
Hanafusa et al., *Biken J.* 2: 85-91 (1959).
Hruby et al., *J. Virol* 29: 705-715 (1979).
Hruby et al., *Proc. Nat'l. Acad. Sci. USA* 76: 1887-1890 (1979).
Lee-Chen et al., *Virology* 163: 64-79 (1988).
Lee-Chen et al., *Virology* 163: 80-92 (1988).
Maxam et al., *Proc. Nat'l. Acad. Sci. USA* 74: 560-564 (1977).
Moss, *Comprehensive Virology*, Fraenkel-Conrat, H. and Wagner, R.R., pp. 405-474 (1974).
Munyon et al., *J. Virol* 5: 32- (1970).
Obert et al., *Biochem. Biophys. Res. Commun.* 44: 362- (1971).
Panicali et al., *J. Virol.* 37: 1000-1010 (1981).
Pennington et al., *J. Virol.* 13: 488-493 (1974).
Rosel et al., *J. Virol.* 56: 830-838 (1985).
Rosel et al., *J. Virol.* 60: 436-449 (1986).
Venkatesan et al., *Cell* 125: 805-813 (1981).
Venkatesan et al., *J. Virol.* 44: 637-646 (1982).
Weaver et al., *Nucl. Acids Res.* 7: 1175-1193 (1979).
Weir et al., *J. Virol.* 51: 662-669 (1984).
Cooper et al., *J. Virol.* 37: 284-294 (1981).
Cooper et al., *J. Virol.* 39: 733-745 (1981).
Venkatesan, *J. Virol.* 37: 738-747 (1981).
Kent, "Isolation and Analysis of the Vaccinia Virus P4B Gene Promoter", *Ph.D. Dissertation, University of Cambridge* (1988).
Paolett et al., *J. Virol.* 33:208-219 (1980).
Wittek et al., *Cell* 21:481-493 (1980).
Paoletti et al., *Proc. Natl. Acad. Sci. USA* 81: 194-196 (1984).
Cheng et al., *J. Virol.* 60: 337-344 (1986).
Coupar et al., *Eur. J. Immunol.* 16: 1479-1487 (1986).
Coupar et al., *J. gen. Virol.* 68: 2299-2309 (1987).
McCarthy et al., *Virology* 59: 59-69 (1974).
Munyon et al., *J. Virology*, pp. 813-820 (Jun. 1971).
Munyon et al., *Federation Proceedings* 31(6) (Nov.-Dec. 1972).
Sam & Dumbell, *Ann. Virol.* {Inst. Pasteur}. 132E, pp. 135-150 (1981).
Weir et al.,*Proc. Natl. Acad. Sci. USA* 79:1210-1214 (1982).

Panicali et al., *Proc. Natl. Acad. Sci. USA* 79: 4927-4931 (1982).
Panicali et al., *Proc. Natl. Acad. Sci. USA* 80: 5364-5368 (1983).
Panicali et al., *Proc. Natl. Acad. Sci. USA* 81: 193-197 (1984).
Moss, *Virology,* pp. 2079-2111, Raven Press (1990).
Hanafusa et al., *Bikens' J.* 2:77-82 (1959).
Fenner et al., *Virology* 11:185-201 (1960).
Boyle et al., *J. gen. Virol.* 67: 1591-1600 (1986).
Boyle et al., *Virus Res.* 10: 343-356 (1988).
Taylor et al., *Vaccine* 6: 497-503 (1988).
Spehner et al., *J. Virol.* 64: 527-533 (1990).
Post et al., *Cell* 25:227-232 (1981).
Peabody et al., *Molec. & Cell Biol.* 6:2704-2711 (1986).
Perez et al., *J. Virol.,* 61: 1276-81 (1987).
Geballe et al., *J. Virol.* 62: 3334-3340 (1988).
Hensel et al., *J. Virol.* 63: 4986-4990 (1989).
Davison et al., *J. Mol. Biol.* 210: 749-769 (1989).
Decision of Opposition Div. regarding Eur. Pat. No. 0110385, including annexes (Oct. 25, 1996).
Pox-Iridovirus Meeting, Participant Housing List (Sep. 20-23, 1982) and Abstracts 1-61.
Moyer et al., *Virol.* 102: 119-32 (1980).
Dumbell et al., *Nature* 286: 29-32 (1980).
Archard et al., *J. Gen. Virol.* 45: 51-63 (1979).
Weir et al., *Proc. Nat'l Acad. Sci. USA* 79: 1210-14 (1982).
Moss et al., *J. Virol.* 40: 387-95 (1981).
Eposito et al., *Virol.* 165: 313-316 (1988).
Boyle et al., *Vir. Res.* 10: 343-56 (1988).
Drillen et al., *Virol.* 160 (203-09 (1987).
Sphener et al., *J. Virol.* 64: 527-33 (1990).
Binns et al., *Isr. J. Vet. Med.* 42: 124-27 (1986).
Fleming et al., *Virol.* 187: 464-71 (1992).
Boursnell et al., *J. Gen. Virol.* 71: 621-28 (1990).
Boursnell et al., *Virol.* 178: 297-300 (1990).
van der Leek et al., *Vet. Rec.* 134: 13-18.
Patel et al., *Proc. Nat'l Acad. Sci. USA* 85: 9431-35 (1988).
Kumar et al., *Arch. Virol.* 112: 139-48.
Pearson et al., *Virol.* 180: 561-66 (1991).
Sam et al., *Ann. Virol.* 132: 135-50 (1981).
L.C. Archard et al., "Restriction Endonuclease Analysis of Red Cowpox Virus and its White Pock Variant", J. gen. Virol., 1979, pp. 51-63, vol. 45.
Basil M. Arif, "The Entomopoxviruses", Advances in Virus Research, pp. 195-213, vol. 29.
Noel Barrett et al., "Large-Scale Production and Purification of a Vaccinia Recombinant-Derived HIV-1 gp160 and Analysis of Is Immunogenicity", AIDS Research and Human Retroviruses, 1989, pp. 159-171, vol. 5, No. 2.
Christine Bertholet et al., "One Hundred Base Paris of 5$\Lambda${\prime}$ Flanking Sequence of a Vaccinia Virus Late Gene are Sufficient to Temporally Regulate Late Transcription", Proceedings of the National Academy of Sciences of the United States of America, 1985, pp. 2096-2100, vol. 82, No. 7.
M.M. Binns, et al., "Prospects for a Novel Genetically Engineered Vaccine Against Infectious Bronchitis", Isr. J. Vet. Med., 1986, pp. 124-127, vol. 42, No. 2.
Michael Boshart et al., "A Very Strong Enhancer is Located Upstream of an Immediate Early Gene of Human Cytomegalovirus", Cell, 1985, pp. 521-530, vol. 41.

M.E.G. Boursnell et al.., "A Recombinant Fowlpox Virus Expressing the Hemagglutinin-Neuraminidase Gene of Newcastle Disease Virus (NDV) Protects Chickens against Challenge by NDV", Virology, 1990, pp. 297-300, vol. 178.

M.E.G. Boursnell et al., "Insertion of the fusion gene from Newcastle disease virus into a non-essential region in the terminal repeats of fowlpox virus and demonstration of protective immunity induced by the recombinant", Journal of General Virology, 1990, pp. 621-628, vol. 71.

David B. Boyle et al., "Fowlpox Virus Thymidine Kinase: Nucleotide Sequence and Relationships to Other Thymidine Kinases", Virology, 1987, pp. 355-365, vol. 156.

David B. Boyle et al., "Construction of recombinant fowlpox viruses as vectors for poultry vaccines", Virus Research, 1988, pp. 343-356, vol. 10.

David B. Boyle et al., "Identification and Cloning of the Fowlpox Virus Thymidine Kinase Gene Using Vaccinia Virus", J. gen. Virol., 1986, pp. 1591-1600, vol. 67.

Steven S. Broyles et al., "DNA-dependent ATPase Activity Associated with Vaccinia Virus Early Transcription Factor", The Journal of Biological Chemistry, The Journal of Biological Chemistry, 1988, pp. 10761-10765, vol. 263, No. 22.

Steven S. Broyles et al., "The Small Subunit of the Vaccinia Virus Early Transcription Factor Contacts the Transcription Promoter DNA", Journal of Virology, 1993, pp. 5677-5680.

Steven S. Broyles et al., "Purification of a Factor Required for Transcription fo Vaccinia Virus Early Genes", The Journal of Biological Chemistry, 1988, pp. 10754-10760, vol. 263, No. 22.

Richard C. Condit et al., "Isolation, Characterization, and Physical Mapping of Temperature-Sensitive Mutants of Vaccinia Virus", Virology, 1984, pp. 429-443, vol. 128.

Robert Drillien et al., "Similar Genetic Organization between a Region of Fowlpox Virus DNA and the Vaccinia Virus Hindlll J Fragment Despite Divergent Location of the Thymidine Kinase Gene", Virology, 1987, pp. 203-209, vol. 160.

K.R. Dumbell et al., "Comparison of white pock (h) mutants of monkeypox virus with parental monkeypox and with variola-like viruses isolated from animals", Nature, 1980, pp. 29-32, vol. 286.

Joseph J. Esposito et al., "Successful Oral Rabies Vaccination of Raccoons with Raccoon Poxvirus Recombinants Expressing Rabies Virus Glycoprotein", Virology, 1988, pp. 313-316, vol. 165.

Joseph J. Esposito et al., "Orthopoxvirus DNA: A Comparison of Restriction Profiles and Maps", Virology, 1985, pp. 230-251, vol. 143.

Falko G. Falkner et al., "*Escherichia coli* gpt Gene Provides Dominant Selection for Vaccinia Virus Open Reading Frame Expression Vectors", Journal of Virology, 1988, pp 1849-1854, vol. 62, No. 6.

Falko G. Falkner et al., "Transient Dominant Selection of Recombinant Vaccinia Viruses", journal of Virology, 1990, pp. 3108-3111, vol. 64, No. 6.

Stephen B. Fleming et al., "In Vivo Recognition of Orf Virus Early Transcriptional Promoters", Virology, 1992, pp. 464-471, vol. 187.

Paul D. Gershon et al., "Early transcription factor subunits are encoded by vaccinia virus late genes", Proc. Natl. Acad. Sci., 1990, pp. 4401-4405, vol. 87.

Peter Gunning et al., "A Human β-actin expression vector system directs high-level accumulation of antisense transcripts",.

F.L. Graham et al., "Transformation of Rat Cells by DNA of Human Adenovirus 5", Virology, 1973, pp. 536-539, vol. 54.

Clayton Hunt et al., "Conserved features of eukaryotic *hsp*70 genes revealed by comparision with the nucleotide sequence of human hsp70", Proc. Natl. Acad. Sci., 1985, pp. 6455-6459, vol. 82.

Stuart N. Isaacs et al., "Reverse Guanine Phosphorisbosyltransferase Selection of Recombinant Vaccinia Viruses", Virology, 1990, pp. 626-630, vol. 178.

Satish Jindal et al., "Vaccinia Virus Infection Induces a Stress Response That Leads to Association of Hsp70 with Viral Proteins", Journal of Virology, 1992, pp. 5357-5362.

Eileen M. Kane et al., "Vaccinia Virus Morphogenesis Is Blocked by a Temperature-Sensitive Mutation in the 17 Gene That Encodes a Virion Component", Journal of Virology, 1993, pp. 2689-2698.

Michael Kriegler, "Retroviral Vectors", Gene Transfer and Expression, pp. 47-56.

Valeri Krougliak et al., "Developement of Cell Lines Capable of Complementing E1, E4, and Protein IX Defective Adenovirus Type 5 Mutants", Human Gene Therapy, 1995, pp. 1575-1586, vol. 6.

Sharad Kumar et al., "Activity of a fowlpox virus late gene promoter in vaccinia and fowlpox virus recombinants", Arch Virol., 1990, pp. 139-148, vol. 112.

Chingfeng Lai et al., "Strucutural and Functional Properties of the 14-kDa Envelope Protein of Vaccinia Virus Synthesized in *Escherichia coli*\*, The Journal of Biological Chemistry", 1990, pp. 22174-22180, Vo. 265, No. 36.

W.H.R. Langridge et al., "Partial Characterization of DNA from Five Entomopoxviruses", Journal of Invertebrate Pathology, 1983, 369-375, vol. 42.

M.L. Van Der Leek et al., Evaluation of swinepox virus as a vaccine vector in pigs using an Aujeszky's disease (pseudorabies) virus gene insert coding for glycoproteins gp50 and gp63, The Veterinary Record, 1994, pp. 13-18.

Michael Mackett et al., "Vaccinia Virus: A Selectable Eukaryotic Cloning and Expression Vector", Proc. Natl. Acad. Scie., 1982, pp. 7415-7419, vol. 79.

Richard Mann et al., "Construction of a Retrovirus Packaging Mutant and Its Use to Produce Helper-Free Defective Retrovirus", Cell, 1983, pp. 153-159, vol. 33.

R.F. Massung et al., "The Molecular Biology of Swinepox Virus", Virology, 1991, pp. 355-364, vol. 180.

Bernard Moss et al., "Deletion of a 9,000-Base-Pair Segment of the Vaccinia Virus Genome That Encodes Nonessential Polypeptides", Journal of Virology, 1981, pp. 387-395, vol. 40, No. 2.

Richard W. Moyer et al., "The White Pock Mutants of Rabbit Poxvirus", Virology, 1980, pp. 119-132, vol. 102.

H.K. Mueller et al., "Comparison of Fice Poxvirus Genomes by Analysis with Restriction Endonucleases *Hind*III, *Bam*I and *Eco*RI", J. gen. Virol., 1977, pp. 135-147, vol. 38.

Eileen Nakano et al., "Molecular Genetics of Vaccinia Virus: Demonstration of Marker Rescue", "Molecular genetics of vaccinia virus: Demonstration of marker rescue", Proc. Natl. Acad. Scie., 1982, pp. 1593-1596, vol. 79.

Dennis Panicali et al., "Construction of Live Vaccines by Using Genetically Engineered Poxviruses: Biological Activity of Recombinant Vaccinia Virus Expressing Influenza Virus Hemagglutinin", Proc. Natl. Acad. Sci., 1983, pp. 5364-5368, vol. 80.

Dennis Panicali et al., "Construction of Poxviruses as Cloning Vectors: Insertion fo the Thymidine Kinase Gene from Herpes Simplex Virus into the DNA of Infectious Vaccinia Virus", proc. Natl. Acad. Sci., 1982, pp. 4927-4931, vol. 79.

Dhavalkumar D. Patel et al., "A poxvirus-derived vector that directs high levels of expression of cloned genes in mammalian cells", Proc. Natl. Acad. Sci., 1988, pp. 9431-9435, vol. 85.

Angela Pearson et al., "The 5' Noncoding Region Sequence of the Choristoneura biennis Entomopoxvirus Spheroidin Gene Fuctions as an Efficient Late Promoter in the Mammalian Vaccinia Expression Ssystem", Virology, 1991, pp. 561-566, vol. 180.

Marion E. Perkus et al., "Cloning and Expression of Foreign Genes in Vaccinia Virus, Using a Host Range Selection System", Journal of Virology, 1989, pp. 3829-3836, vol. 63, No. 9.

David P. Pickup et al., "Sequence of terminal regions of cowpox virus DNA: Arrangement of repeated and unique sequence elements", Proc. Natl. Acad. Sci., 1982, pp. 7112-7116, vol. 79.

C.T. Prideaux et al., "Fowlpox virus polypeptides: sequential appearance and viron associated polypeptides", Arch Virol., 1987, pp. 185-199, vol. 96.

P.L. Foley et al., "Winepox Virus as a Vector for the Delivery of Immunogens", Annals of the New York Academy of Sciences, 1991, pp. 220-222, vol. 646.

C.K. Sam et al., "Expression of Poxvirus DNA in Coinfected Cells and Marker Rescue of Thermosensitive Mutants by Subgenomic Fragments of DNA", Ann. Virol., 1981, pp. 135-150, vol. 132E.

W.M. Schnitzlein et al., "Genomic and antigenic characterization of avipoxviruses", Virus Research, 1988, pp. 65-76, vol. 10.

Geoffrey L. Smith et al., "Construction and Characterization of an Infectious Vaccinia Virus Recombinant That Expresses the Influenza Hemagglutinin Gene and Induces Resistance to Influenza Virus Infection in Hamsters", Proc. Natl., Acad. Sci., 1983, pp. 7155-7159, vol. 80.

Daniele Spehner et al., "Construction of Fowlpox Virus Vectors with Intergenic Insertions: Expression of the β-Galactosidase Gene and the Measles Virus Fusion Gene", Journal of Virology, 1990, pp. 527-533, vol. 64, No. 2.

Jill Taylor et al., "Protective immunity against avian influenza inducted by a fowlpox virus recombinant", Vaccine, 1988, pp. 504-508, vol. 6.

Harry Towbin et al., "Electrophoretic transfer of proteins from polyacrylamide gets to nitrocellulose sheets: Procedure and some applications", Proc. Natl. Acad. Sci., 1979, pp. 4350-4354. vol. 76. No. 9.

Sundararajan Venkatesan et al., "Distinctive Nucleotide Sequences Adjacent to Multiple Initiation and Termination Sites of an Early Vaccinia Virus Gene", Cell, pp. 805-813, vol. 125.

Q. Wang et al., "A packaging cell line for propagation of recombinant adenovirus vectors containing two lethal gene-region deletions", Gene Therapy, 1995, pp. 775-783, No. 2.

Jerry P. Weir et al., "Mapping of the Vaccinia Virus Thymidine Kinase Gene by Marker Rescue and by Cell-Free Translation of Selected mRNA", Proc. Natl. Acad. Sci., 1982, pp. 1210-1214, vol. 79.

Jerry P. Weir et al., "Use of a Bacterial Expression Vector to Identify the Gene Encoding a Major Core Protein of Vaccinia Virus", Journal of Virology, 1985, pp. 534-540, vol. 56, No. 2.

Jerry P. Weir et al., "Regulation of Expression and Nucleotide Sequence of a Late Vaccinia Virus Gene", Journal of Virology, 1984 pp. 662-669, vol. 51, No. 3.

Michael Wigler et al., "Transfer of Purified Herpes Virus Thymidine Kinase Gene to Cultured Mouse Cells", Cell, 1977, pp. 2230-2232, vol. 11.

Riccardo Witek et al., "Mapping of a Gene Coding for a Major Late Structural Polypeptide on the Vaccinia Virus Genome", Journal of Virology, 1984 pp 371-378, vol. 49, No. 2.

Celeste Yanisch-Perron et al., "Improved M13 Phage Cloning Vectors and Host Strains: Nucleotide Sequences of the M13mp18 and pUC19 Vectors", Gene, 1985, pp. 103-119, vol. 33.

Yifan Zhang et al., "Immature Viral Envelope Formation Is Interrupted at the Same Stage by *Iac* Operator-Mediated Repression of the Vaccinia irus D13L Gene and by the Drug Rifampicin", Virology, 1992, pp. 643-654, vol. 187.

Jill Taylor et al., "Fowlpox virus as a vector in non-avian species", Vaccine, 1988, pp. 466-468, vol. 6.

"Vaccinia Virus as a Vector for Vaccine Antigens", pp. 353-377.

McFadden et al., "Biogenesis poxviruses: mirror-image deletions in vaccinia virus DNA", Dialog(R) File: Medline (R), Apr. 7, 2002, Sep. 1979, 18 (1) p101-8. ISSN 0092-8674.

Moss B., et al., "Deletion of a 9,000-base-pair segment of the vaccinal virus genome that encodes nonessential polypeptides", Dialog(R) File: Medline(R), Apr. 7, 2003, Nov. 1981, 40 (2) p387-95, ISSN 0022-538X.

Moyer, R.W. et al., "The white pock mutants of rabbit poxvirus. I. Spontaneous host range mutants contain deletions", Dialog(R) File: Medline(R), Jan. 7, 2005, Apr. 15, 1980, 102 (1) p119-32, ISSN 0042-6822.

Smith, G.L. et al., "Infectious vaccinia virus recombinants that express hepatitis B virus surface antigen", Dialog(R) File: Medline(R), 6/7/10, Apr. 7, 1983, 302 (5908) p490-5, ISSN 0028-0836.

Weir, J.P., et al., "Nucleotide sequence of the vaccinia virus thymidine kinase gene and the nature of spontaneous frameshift mutations", Dialog(R) File: Medline(R), 6/7/7, May 1983, 46 (2) p530-7, ISSN 022-538X.

John Holowczak et al., Pox-Iridovirus Meeting, Sep. 20-23, 1982, Opposition to EP-B1-0 110 385, including abstract pp. 1-61.

Paoletti et la. V. Moss et al., Interference Record, U.S. Patent & Trademark Office Before Board of Patent Appeals and Interferences, Interference No. 103,399,.

Decision Revoking the European Patent (Article 102(1) EPC), Applic. No. 83111976.3-2110/0110385, Oct. 25, 1996.

Moss Record, Paoletti et al. v. Moss et al., U.S. Patent & Trademark Office Before Board of Patent Appeals and Interferences, Interference No. 103,399, Oct. 31, 2001.

Before the Board of Patent Appeals and Intereferences, Paoletti and Panicali, Compliant, U.S. District Court for the District of Columbia, Aventis Pasteur, Inc., v. U.S. Dept. of Health & Human Services et al., Case No. 1:02CV01442, Jul. 26, 2002.

Notice to Court Concerning Mail Service at United States Attorney's Office, Pasteur, Inc. v. U.S. Dept. of Health & Human Services, U.S. District Court for the District of Columbia, Action No. 02-1442(LFO), Nov. 12, 2002.

Aventis' Memorandum of Points and Authorities in Opposition to Defendants' Motion to Dismiss Part of the Complaint for Lack of Jurisdiction; for a More Definite Statement of the Remaining Claim; and to Amend the Case Caption, Pasteur, Inc. v. U.S. Dept. of Health & Human Services, Action No. 02-1442(LFO), Dec. 6, 2002.

Voluntary Dismissal by Plaintiff Pursant to FRCP 41(a)(1), Pasteur, Inc. v. U.S. Dept. of Health & Human Services, Action No. 02-1442(LFO), Mar. 31, 2003.

Paoletti et al. v. Moss et al., Paoletti et al. Motion Under 37 CFR §1.633(a) and (g) For Judgment On Ground That Moss et al. claims Not Patentable to Moss et al. for Failing to Point Out and Distinctly Claim the Subject Matter of the Invention, Paoletti, et al. v. Moss, et al., U.S. Patent and Trademark Office Before the Board of Patent Appeals and Interferences, No. 103,399, Mar. 13, 1995.

Paoletti et al. v. Moss et al., Paoletti et al. Motion Under 37 CFR §1.633(a) and (g) for Judgment on Ground that Moss et al. Claims Are Not Patentable to Moss et al. for Failing to Provide and Enabling Disclosure and an Adequate Written Description, U.S. Patent and Trademark Office Before the Board of Patent Appeals and Interferences, No. 103,399, Mar. 15, 1995.

Paoletti et al. v. Moss et al., Paoletti et al. Motion Under 37 CFR §1.633 and 1.637 for Judgment on Ground that Moss et al. Claims Not Patentable to Moss et al., U.S. Patent and Trademark Office Before the Board of Patent Appeals and Interferences, No. 103,399, Mar. 16, 1995.

Paoletti et al. v. Moss et al., Paoletti et al. Under 37 CFR §§1.633(g) and 1.637(g) Attacking Benefit Accord Moss et al., U.S. Patent and Trademark Office Before the Board of Patent Appeals and Interferences, No. 103,399, Mar. 16, 1995.

Paoletti et al. v. Moss et al., Opposition by Moss et al. to Paoletti et al. Motion Under 37 CFR §§1.633(a) and (g) for Judgment on the Ground that Moss et al. Claims are not Patentable to Moss et al. for failing to Provide an Enabling Disclosure and an Adequate Written Description, U.S. Patent and Trademark Office Before the Board of Patent Appeals and Interferences, No. 103,399, Apr. 13, 1995.

Paoletti et al. v. Moss et al., Opposition by Moss et al. to Paoletti et al. Motion Under 37 CFR §§1.633(a) and (g) for Judgment on the Ground that Moss et al. Claims are not Patentable to Moss et al. for Failing to Point out and Distinctly Claim the Subject Matter of the Invention, U.S. Patent and Trademark Office Before the Board of Patent Appeals and Interferences, No. 103,399, Apr. 13, 1995.

Paoletti et al. v. Moss et al., Opposition by Moss et al. to Paoletti et al. Motion Under 37 CFR §§1.633(g) and 1.637 (g) attacking Benefit Accorded Moss et al., U.S. Patent and Trademark Office Before the Board of Patent Appeals and Interferences, No. 103,399, Apr. 13, 1995.

Paoletti etal.. v. Moss et al., Opposition by Moss et al. to Paoletti et al. Motion Under 37 CFR §§1.633 and 1.637 For Judgment on the Ground that Moss et al. Claims Are Not Patentable to Moss et al., U.S. Patent and Trademark Office Before the Board of Patent Appeals and Interferences, No. 103,399, Apr. 13, 1995.

Paoletti et al. v. Moss et al., Opposition by Moss et al. to Paoletti et al. Motion Under 37 CFR §§1.633(c)(1) and 1.637(c)(1) to Substitute A Count, U.S. Patent and Trademark Office Before the Board of Patent Appeals and Interferences, No. 103,399, Apr. 21, 1995.

Paoletti et al. v. Moss et al., Opposition by Moss et al. Motion Under 37 C.F.R. §§1.633(g) and 1.637(g) Attacking Benefit Accorded Moss et al., U.S. Patent and Trademark Office Before the Board of Patent Appeals and Interferences, No. 103,399, Apr. 21, 1995.

Paoletti et al. v. Moss et al., Reply to Opposition by Moss et al. to Paoletti et al. Motion Under Under 37 C.F.R. §§1.633 and 1.637 for Judgment on the Ground that Moss et al. Claims are Not Patentable to Moss et al., U.S. Patent and Trademark Office Before the Board of Patent Appeals and Interferences, No. 103,399, Apr. 21, 1995.

Paoletti et al. v. Moss et al., Paoletti et al.'s Opposition to Moss et al.'s Contigent Motion under 37 CFR §1.633(f) and §1.637(f) for Benefit of Their Earlier Application, U.S. Patent and Trademark Office Before the Board of Patent Appeals and Interferences, No. 103,399 Jul. 28, 1998.

Paoletti et al. v. Moss et al., Opposition by Moss et al. to Paoletti et al. Paper Stylized As: "Request for Testimony Period and Opposition to Sua Sponte Holdings", U.S. Patent and Trademark Office Before the Board of Patent Appeals and Interferences, No. 103,399, May 1, 1998.

Paoletti et al. v. Moss et al., Opposition by Moss et al. to Paoletti et al. Paper Stylized As: "Request for Final Hearing and Opposition to Sua Sponte Holdings", U.S. Patent and Trademark Office Before the Board of Patent Appeals and Interferences, No. 103,399, May 1, 1998.

Paoletti et al. v. Moss et al., Opposition by Moss et al. to Paoletti et al. Paper Stylized As: "Motion Under 37 C.F.R. §1.633(c) & 1.637(C)(2)" (Claim Motion No. 1), U.S. Patent and Trademark Office Before the Board of Patent Appeals and Interferences, No. 103,399, May 1, 1998.

Paoletti et al. v. Moss et al., Opposition by Moss et al. to Paoletti et al. Paper Stylized As: "Request for Testimony Period and Final Hearing on Issue of Derivation by moss and Opposition to Sua Sponte Holdings", U.S. Patent and Trademark Office Before the Board of Patent Appeals and Interferences, No. 103,399, May 1, 1998.

Paoletti et al. v. Moss et al., Opposition by Moss et al. to Paoletti et al. Paper Stylized As: "Motion Under 37 C.F.R. §1.633(c)(1) & 1.637(c)(1)" to Amend the Count, U.S. Patent and Trademark Office Before the Board of Patent Appeals and Interferences, No. 103,399, May 1, 1998.

Paoletti et al. v. Moss et al., Opposition by Moss et al. to Paoletti et al. Paper Stylized As: "Motion Under 37 C.F.R. §1.633(c) & 1.637(c)(2)" (Claim Motion No. 2), U.S. Patent and Trademark Office Before the Board of Patent Appeals and Interferences, No. 103,399, May 1, 1998.

Paoletti et al. v. Moss et al., Opposition by Moss et al. to Paoletti et al. Paper Stylized As: "Motion Under 37 C.F.R. §1.633(f) & 1.637(f)", U.S. Patent and Trademark Office Before the Board of Patent Appeals and Interferences, No. 103,399, May 1, 1998.

Paoletti et al. v. Moss et al., Contigent Motion by Moss et al. Under 37 CFR §1.633(i) & 1.637(a) and (f) to be Accorded Benefit of the Filing Date of Earlier Applications, in the Event Paoletti Motion to Amend the Count [Proposed Count B] is Granted (Contingent Motion No. 2), U.S. Patent and Trademark Office Before the Board of Patent Appeals and Interferences, No. 103,399, May 1, 1998.

Paoletti et al. v. Moss et al., Request for Testimony Period and Opposition to Sua Sponte Holdings, U.S. Patent and Trademark Office Before the Board of Patent Appeals and Interferences, No. 103,399, Jan. 13, 1998.

Paoletti et al. v. Moss et al., Request for Final hearing and Opposition to Sua Sponte Holdings, U.S. Patent and Trademark Office Before the Board of Patent Appeals and Interferences, No. 103,399, Jan. 13, 1998.

Paoletti et al. v. Moss et al., Motion Under 37 CFR §§1.633(c) & §1.637(c)(2), U.S. Patent and Trademark Office Before the Board of Patent Appeals and Interferences, No. 103,399, Jan. 13, 1998.

Paoletti et al. v. Moss et al., Declaration of Marion Perkus, U.S. Patent and Trademark Office Before the Board of Patent Appeals and Interferences, No. 103,399, Jan. 13, 1998.

Paoletti et al. v. Moss et al., Request for Testimony Period and Final Hearing on Issue of Derivation by Moss and Opposition to Sua Sponte Holdings, U.S. Patent and Trademark Office Before the Board of Patent Appeals and Interferences, No. 103,399, Jan. 13, 1998.

Paoletti et al. v. Moss et al., Order Sua Sponte Holding Under 37 CFR §1.633(b), U.S. Patent and Trademark Office Before the Board of Patent Appeals and Interferences, No. 103,399, Feb. 13, 1997.

Paoletti et al. v. Moss et al., Reply by Moss et al. to Paoletti et al. Opposition to Contigent Motion by Moss et al. Under 37 C.F.R. §1.633(l), and §1.637(a) and (f) to be Accorded Benefit of the Filing Date of Earlier Applications, in the Event Paoletti Motion for Substitute Count is Granted, U.S. Patent and Trademark Office Before the Board of Patent Appeals and Interferences, No. 103,399, May 3, 1995.

Paoletti et al. v. Moss et al., Paoletti et al.'s Response and Opposition to APJ Metz' Sua Sponte Order of No Interference-In-Fact, U.S. Patent and Trademark Office Before the Board of Patent Appeals and Interferences, No, 103,399, Mar. 16, 2001.

Paoletti et al. v. Moss et al., Final Decision, U.S. Patent and Trademark Office Before the Board of Patent Appeals and Interferences, No. 103,399, May 20, 2002.

Andrew J. Davidson et al., "Structure of Vaccinia Virus Early Promoters", J. Mol. Biol., J. Mol. Biol., 1989, pp. 749-769, vol. 210.

Ann M. Moriarty et al., "Expression of the hepatitis B virus surface antigen gene in cell culture by using a simian virus 40 vector", Proc. Natl. Acad. Sci. USA, 1981, pp. 2606-2610, vol. 78, No. 4.

Barbara E.H. Coupar et al., "Effect in vitro Mutations in a Vaccinia Virus Early Promoter Region Monitored by Herpes Simplex Virus Thymidine Kinase Expression in Recombinant Vaccinia Virus", J. gen. Virol., 1987, pp. 2299-2309, vol. 68.

David B. Boyle et al., "Multiple-cloning-site plasmids for the rapid contruction of recombinant poxviruses", Gene, 1985, pp. 167-177, vol. 35.

Enzo Paoletti et al., "Construction of live vaccines using genetically engineered poxviruses: Biological activity of vaccinia virus recombinants expressing the hepatitis B virus surface antigen and the herpes simplex virus glycoprotein D", Proc. Natl. Acad. Sci., 1984, pp. 193-197, vol. 81.

Girish J. Kotwal et al., "Analysis of a Large Cluster of Nonessential Genes Deleted from a Vaccinia Virus Terminal Transposition Mutant", Virology, 1988, pp. 524-537, vol. 167.

Judy Sprague et al., "Expression of a Recombinant DNA Gene Coding for the Vesicular Stomatitis Virus Nucleocapsid Protein", Journal of Virology, 1983, pp. 773-781, vol. 45, No. 2.

Michael J. Wagner et al., "Nucleotide sequence of the thymidine kinase gene of herpes simplex virus type 1", Proc. Natl. Acad. Sci., 1981, pp. 1441-1445, vol. 78, No. 3.

Scott J. Goebel et al., "Appendix to The Complete DNA Sequence of Vaccinia Virus", Virology, 1990, pp. 517-563, Vol. 179.

Sudararajan Venkatesan et al., "Distinctive Nucleotide Sequences Adjacent to Multiple Initiation and Termination Sites of an Early Vaccinia Virus Gene", Cell, 1981, pp. 805-813, vol. 125.

Dennis Panicali et al., "Two Major DNA Variants Present in Serially Propagated Stocks of the WR Strain of Vaccinia Virus", Journal of Virology, 1981, pp. 1000-1010.

* cited by examiner

RECOMBINANT POXVIRUSES HAVING FOREIGN DNA EXPRESSED UNDER THE CONTROL OF POXVIRUS REGULATORY SEQUENCES

This application is a continuation of application Ser. No. 07/987,546, filed Dec. 7, 1992, which is a continuation of application Ser. No. 07/539,169, filed Jun. 18, 1990, now abandoned, which is a continuation of application Ser. No. 07/072,455, filed Jul. 13, 1987, now abandoned, which is a continuation-in-part of application Ser. No. 06/555,811, filed Nov. 28, 1983, now abandoned, and a continuation-in-part of application Ser. No. 06/445,892, filed Dec. 1, 1982, now abandoned, and a continuation-in-part of application Ser. No. 06/445,451, filed Nov. 30, 1982, now abandoned. Said application 06/445,892, filed Dec. 1, 1982, is a continuation-in-part of said application 06/445,451, filed Nov. 30, 1982, Said application 06/555,811, filed Nov. 28. 1983 is a continuation-in-part of said application 06/445,892, filed Dec. 1. 1982, and said application 06/445,451, filed Nov. 30, 1982. Each of these applications are hereby incorporated by reference.

This invention provides recombinant vaccinia virus synthetically modified by insertion of a chimeric gene containing vaccinia regulatory sequences or DNA sequences functionally equivalent thereto flanking DNA sequences which to nature are not contiguous with the flanking vaccinia regulatory DNA sequences. It has been found that the recombinant virus containing such a chimeric gene is surprisingly effective in expressing the foreign gene.

Recombinants of the present invention have been useful as vaccines providing antibodies effective against the organisms from which the foreign DNA of the chimeric gene was derived. Some examples of such foreign genes include DNA genes or DNA copies of RNA genes from hepatitis B virus, hepatitis A virus, hepatitis non-A, non-B virus, influenza virus, herpesvirus, cytomegalovirus, adenoviruses, parvoviruses, foot and mouth disease virus, poliovirus, measles virus, rabies virus, coronaviruses, coxsackieviruses and pathogenic bacteria, rickettsia protozoa, and metazoa. In accordance with the present invention, cells infected with poxvirus recombinants are also used to prepare the foreign gene product.

In considering the development of vaccinia virus or other poxviruses as infectious expression vectors, the following biological characteristics of these agents were taken into account: evidence that vaccinia virus has evolved its own transcriptional regulatory sequences: its large genome size; and lack of infectivity of isolated viral DNA.

In the preferred embodiment of the invention expression of foreign DNA is obtained by forming chimeric genes consisting of a vaccinia virus transcriptional regulatory sequence and an uninterrupted protein coding sequence of a foreign gene. The vaccinia virus transcriptional regulatory sequence consists of a DNA segment that precedes and may include the site at which RNA synthesis begins. In the description which follows, sequences that positively regulate the transcription of a gene may be referred to as a "promoter." The foreign gene protein coding sequence may include the site corresponding to initiation of translation and will be referred to hereinafter as the "foreign gene." By using the translational initiation site of the foreign gene in accordance with the present invention, codon phasing and potential problem associated with the biological activity of fusion proteins are avoided if desired. The chimeric gene is flanked by DNA from a known non-essential region of the vaccinia virus genome that will ultimately allow homologous recombination to occur. The present invention thus provides a general method of expressing foreign genes. Plasmids can be constructed that contain multiple restriction endonuclease sites next to the vaccinia virus promoter and that contain the flanking vaccinia virus DNA as well as the plasmid origin of replication and antibiotic resistance gene. The plasmids are then cleaved with an appropriate restriction endonuclease to form ligatable termini, and a foreign gene with complementary termini is ligated next to the vaccinia virus promoter. The plasmid containing the chimeric gene and flanking vaccinia virus DNA is used to transform bacteria and then is purified from the transformed bacteria.

The plasmid containing the chimeric gene flanked by vaccinia virus DNA is then used in accordance with the present invention under transfecting conditions to transfect cells that have been infected with vaccinia virus or another compatible poxvirus. When homologous recombination and replication are allowed to occur, the chimeric gene is inserted into the vaccinia virus genome at the position specified by the flanking DNA used. It is important to use flanking DNA from a non-essential region of the genome so that infectivity will not be destroyed.

BACKGROUND OF THE INVENTION

Recombinant DNA technology has made it possible to express genes of one organism within another. The prior art shows that several virus groups including the papovaviruses, papilloma viruses, adenoviruses, and retroviruses have been employed as eukaryotic molecular cloning and expression vectors. The relatively small sizes of these virus genomes have facilitated the in vitro construction of recombinant DNA molecules. However, they generally exhibit a limited host range, provide severe limitations on the amounts of DNA that can be accommodated and suffer loss of infectivity upon insertion of foreign DNA. Although genetic engineering of larger viruses, such as poxviruses, is more difficult, such vectors could have the advantage of greater capacity and potential of retaining infectivity in a wide range of host cells. For poxviruses such as vaccinia virus, such recombinants may lead to the development of live virus vaccines.

Since vaccinia virus is the best studied member of the poxvirus group, it will be described here. Vaccinia virus has a very broad host range in vitro and in vivo and has been used world-wide as an effective vaccine against variola, a related poxvirus that causes smallpox. Vaccinia is a large virus containing a linear double-stranded DNA genome with a molecular weight of about 122 million, equivalent to more than 180,000 base pairs. The virus uses its own enzymes for transcription and replication within the cytoplasm of infected cells. Nucleotide sequence data indicate that the transcriptional regulatory signals encoded in the vaccinia virus genome are distinct from those used by eukaryotic cells. The invention described here takes into account both the large size of the poxvirus genome and its unique transcriptional regulatory signals.

References which relate to the subject invention are Venkatesan, Baroudy and Moss, Cell 125: 805–813 (1981); Venkatesan, Gershowitz and Moss, J. Virol, . 44: 637–646 (1982); Bajszar, Wittek, Weir and Moss, J. Virol, . 45: 62–72 (1983); Weir and Moss, J. Virol, . 46: 530 (1983); Moss, Winters and Cooper, J. Virol, , 40: 387–395 (1981); Panicali and Paoletti, Proc. Natl. Acad. Sci. USA 79: 4927–4931 (1982); Mackett, Smith and Moss, Proc. Natl. Acad. Sci. USA 79: 7415 (1982); Cohen and Boyer, U.S. Pat. No. 4,237,224; Valuenzuela et al., Nature 298: 347–350 (1982);

Moriarity et al., *Proc. Natl. Acad. Sci. USA* 78: 2606–2610 (1981); Liu et al., DNA 1: 213–221 (1982); Weir, Bajszar and Moss, *Prot. Natl. Acad. Sci USA* 79: 1210 (1982).

DEPOSITION OF MATERIALS

Samples of plasmids and vaccinia virus used in this invention are deposited in the American Type Culture Collection in a manner affording permanence and availability prescribed by MPEP §608.01 (p). The accession numbers are: pGS20 transformed *E. coli*, ATCC #39249; pHBs, 4 transformed *E. coli*, 039250; bHBs, 4, #VR2055; pGS36, #39504; vInf1, #VR2079. Influenza virus A/Jap/305/57 is deposited in the Research Resources Branch of the National Institute of Allergy and Infectious Diseases at the National Institutes of Health, Bethesda. Maryland, under the same conditions described above.

DETAILED DESCRIPTION OF THE INVENTION

Figure 1:
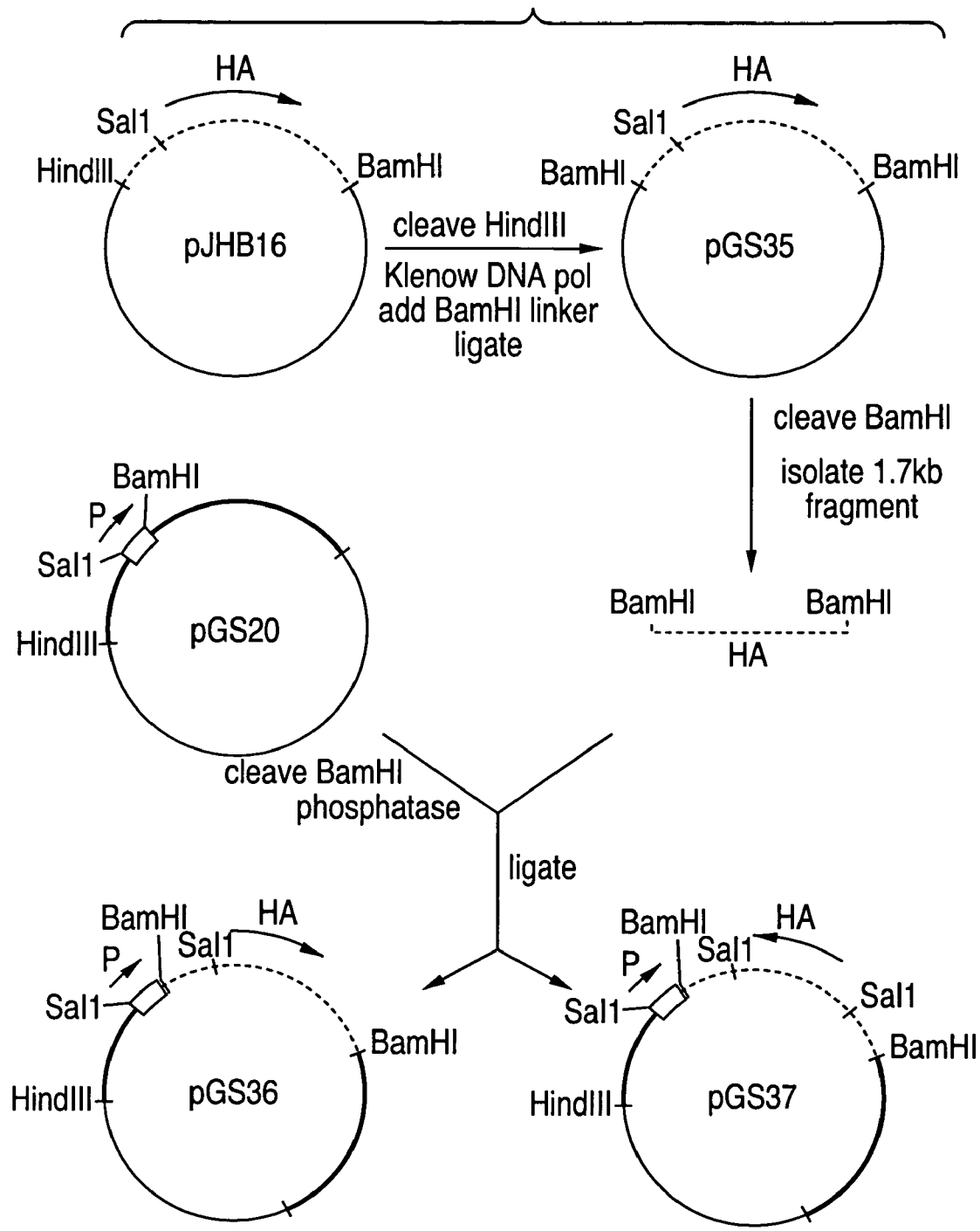
FIG. 1. Construction of a chimeric gene containing the transcriptional regulatory signals and RNA start site of an early vaccinia virus gene.

The invention requires the steps of:
I. Preparation of vector such as a plasmid containing poxvirus promoter, sites for insertion of a foreign gene, and poxvirus DNA flanking sequences.
II. Preparation and insertion of foreign gene into a plasmid or equivalent vector to form chimeric gene.
III. Transfection of cells with the vector containing chimeric gene.
IV. Isolation of recombinant poxvirus and detection of foreign gene product.
V. Infection of susceptible cells or animals with poxvirus recombinants.

This description exemplifying manipulation of the vaccinia virus to provide useful recombinants are provided as exemplary of methods readily applicable to poxvirus. As will be readily apparent to those of ordinary skill in the art. Changes and modifications practiced by or known to those in the art are within the scope of the invention.

1. Preparation of plasmid vector containing vaccinia virus promoter, sites for insertion of a foreign gene, and vaccinia virus DNA flanking sequences.

The vehicle used to assemble the insertion vector may be any convenient plasmid, cosmid or phage. Plasmids constructed for use include pBR322, pBR325, 1 pBR328, pUC7, pUC8, or pUC9 described herein. The vaccinia virus DNA segment used to promote transcription of the foreign gene contained nucleotide sequences according and including the start site of an RNA. The nucleotide sequence and a precise transcriptional map of this region was needed for application of this method. When a convenient restriction endonuclease site preceded the RNA start site and another occurred after the RNA start site but before the first ATG or translational initiation colon, the promoter segment was excised by restriction endonuclease digestion and isolated by standard methods such as agarose gel electrophoresis. When a convenient restriction endonuclease site was not available, it was necessary to use other methods such as cleaving beyond the desired site and removing extra nucleotides with an exonuclease such as Bal, 31. The promoter segment directly or after modification of its ends was ligated to a plasmid that had been cleaved with a restriction endonuclease to provide compatible ligatable termini. Ligation of cohesive or blunt ends followed standard procedures. Additional restriction endonuclease sites were placed next to the promoter by inserting the promoter into a plasmid such as pUC9 that already has multiple insertion sites, however ligation of synthetic polynucleotides should also be possible. The plasmid containing the promoter was used to transform bacteria and then purified. Restriction endonucleases were used to cut out the promoter with adjacent restriction endonuclease sites and the DNA fragment was purified using conventional methods.

The DNA used to flank the promoter and added restriction endonuclease sites was derived from a non-essential region of the vaccinia virus genome. Examples of such non-essential regions include the thymidine kinase gene and a region of at least 9,000 base-pairs (bp) that is proximal to the left inverted terminal repetition. DNA containing the non-essential region was excised by restriction endonuclease cleavage and purified by agarose gel electrophoresis or other conventional methods. The segment was then ligated to plasmid DNA that had been cleaved by a endonuclease to give complementary ligatable termini. The plasmid containing the vaccinia virus DNA was used to transform bacteria and then purified. An appropriate restriction endonuclease was used to cleave the non-essential segment of the vaccinia virus DNA within the plasmid so that it could be ligated to the previously isolated promoter fragment. In this manner or by variations of this procedure, a plasmid was obtained that has a vaccinia virus promoter with adjacent restriction endonuclease sites flanked by a non-essential segment of vaccinia virus DNA. Since this plasmid retained the plasmid origin of replication and antibiotic resistance gene, it was used to transform bacteria and replicated.

II Preparation and insertion of foreign gene into plasmid vector to form a chimeric gene.

A segment of DNA containing a foreign gene or a cDNA copy of a foreign gene was obtained. The DNA segment was cleaved with restriction endonucleases at a site preceding the translational initiation codon and distal to the end of the protein coding sequences. When appropriate sites mare not present, then it was necessary to cleave beyond the desired site and use an exonuclease such as Bal31 to remove extra nucleotides. For optimal expression, the first ATG in the segment was used to initiate translation of the desired gene. Since there is no evidence for splicing of vaccinia virus RNAs, continuous protein coding sequences was used.

The plasmid constructed in part I of this section was cleaved at a restriction endonuclease site next to the promoter. The protein coding segment of the foreign gene was ligated directly to the promoter when it had complementary termini or after modification of its ends. The plasmid was used to transform bacteria and then purified. When the foreign gene was insertable in more than one orientation, it was necessary to analyze by restriction endonuclease digestion and gel electrophoresis or nucleotide sequencing to check that the proper one was obtained. The desired plasmid had the promoter adjacent to the start of the foreign gene.

III Transfection of cells with plasmid containing chimeric gene.

Plasmids containing chimeric genes flanked by DNA from non-essential regions of the vaccinia virus genome were used to transfect cells that were already infected with vaccinia virus. The chimeric gene was inserted into the vaccinia virus genome by homologous recombination. Typically, confluent monolayers of BSC-1, TX$^-$143, or other cells in bottles with a 25 cm$^2$ bottom surface area were infected with 0.01 to 0.05 plaque forming units (pfu) per cell of vaccinia virus. Approximately 1 µg of plasmid DNA with or without 1 µg of vaccinia virus DNA and 20 µg of calf thymus DNA or other carrier DNA was mixed in 1 ml of 0.1% dextrose, 0.14 M NaCl, 5 mM KCl, 1 mM Na$_2$HPO$_4$, 20 mM Napes, (pH 7.05) and precipitated by addition of CaCl$_2$ to a final concentration of 125 mM. The mixture was agitated gently and allowed to remain at room temperature for about 45 min. Two hr after infection, 0.8 ml of the fine suspension was added to an Infected monolayer from which medium had been removed. After 30 min, 8 wt of Eagle or other tissue culture medium containing 8% fetal bovine serum was added to each bottle and the incubation was continued at 37° C. for 3.5 more hr. At 6 hr after infection, fresh medium containing 8% fetal bovine serum was added and incubation was continued for 48 hr. At this time, the infected cells were scraped off the bottle, centrifuged, resuspended in tissue culture medium and homogenized to break the cells and liberate virus.

IV. Isolation of recombinant vaccinia virus and detection of foreign gene product.

Virus from transfected cells consisted of a population of which only a small percentage were recombinants. A variety of selective and non-selective methods were used to isolate these recombinants.

Selective procedures depended on the ability or recombinants to replicate under conditions that inhibited the original virus. One selective method involved the inactivation of the vaccinia virus TK gene. This was achieved by using DNA from the vaccinia virus TK gene to flank the chimeric gene. When homologous recombination occurred, the chimeric gene was inserted into the TK gene of virus DNA and the recombinants exhibited a TK negative (TK$^-$) phenotype. Selective conditions for isolation of TK$^-$ vaccinia virus was achieved by plaquing the virus in monolayers of TK$^-$ negative cells such as TK$^-$143 cells with 25 µg/ml of 5-bromodeoxyuridine (BUdR) in the 1% low melting agar overlay. After 48 to 72 hr at 37° C. in a 5% Co$_2$ humidified atmosphere, plaques were detected by staining with 0.005% neutral red. Typically more than 30% of the TK$^-$ plaques consisted of recombinants and the remainder were spontaneous TK$^-$ mutants of vaccinia virus.

A second selective method was used when TK$^-$ cells were infected with TK$^-$ mutants of vaccinia virus and then transfected with plasmids that contained a chimeric herpesvirus TK gene. [The TK$^-$ mutants of vaccinia virus were obtained by infecting TK$^-$ 143 cells with vaccinia virus in the presence of 25 µg/ml of BUdR. The TK$^-$ negative mutants were then plaqued at least 2 times in succession in TK$^-$143 cells in the presence of BUdR]. Recombinants expressing herpesvirus TK were selected by plaque assay on TK143 cells with a 1% low melting agar overlay containing Eagle medium and 8% fetal bovine serum, 100 µM thymidine, 50 (pH adenosine, 50 (pH guanosine, 10 (pH glycine, 1 (pH methotrexate. After 48 to 72 hr at 37° C. in a 5% CO$_2$, humidified atmosphere, the plaques were detected by staining with neutral red.

Non-selective methods that depend on identification of virus plaques that contain the foreign gene were also used. In addition, such methods were used to confirm the identity of recombinants even after isolation by selective methods.

DNA—DNA hybridization was used to identify plaques formed by recombinant virus. One method was referred to as dot blot hybridization. In this procedure, virus obtained following transfection of infected cells with chimeric plasmids was plaqued on cell monolayers with a 1% agar overlay. After 48 to 72 hr, the plaques were detected by staining with neutral red. Virus within individual plaques were picked using a sterile Pasteur pipette and used to infect cell monolayers in 16 mm diameter wells of microtiter dishes. After 48 hr incubation at 37° C., the cells were scraped, lysed by three freeze-thaw cycles, and collected on nitrocellulose sheets by filtration using a micro-sample manifold (Schleicher and Scnuell, N H). The filter was washed with 100 mM NaCl, 50 mM Tris-HCl (pH 7.5), blotted three times on successive Whatman 3 MM papers saturated with (1) 0.5 M NaOH, (2) 1 M Tris-HCl (pH 7.5), and (3) 2×SSC (SSC is 0.15 M NaCl, 0.015 M sodium citrate), baked at 80° C. for 2 hr and then incubated with 5×Oenhardt's solution [Denhardt, *Biochem. Biophys. Res. Commun.*, , 23:641–646 (1966)], supplemented with 0.1 mg/ml of denatured salmon sperm DNA in 4×SSC at 65° C. for 4 hr. The foreign DNA, labeled with $^{32}$P by nick translation, and sodium dodecyl sulfate (SDS) at a final concentration of 0.1% were added and hybridization continued for 12 hr. The filter was washed twice for 15 min at 65° C. with 2×SSC/0.1% SDS and then with 0.2×SSC/0.1% SDS. An autoradiograph was made by placing the filter next to X-ray film and the presence of dark spots on developed film identified recombinant virus. Another method of DNA—DNA hybridization used was described by Villarreal and Berg [*Science* 196:183–185 (1977)]. In this method, a replica of virus plaques was made by placing a nitrocellulose filter directly on the cell monolayer. DNA—DNA hybridization was carried out as above and, after location of plaques containing recombinant virus, residual virus was eluted from the agar that originally overlayed the plaques.

Additional methods that depend on expression of the foreign gene were also used to identify plaques. In one case, $^{125}$I-labeled antibodies to the product of the foreign gene were incubated with the cell monolayer containing virus plaques. Plaques containing recombinant virus were then identified by autoradiography. When the herpesvirus thymidine kinase was expressed, recombinant plaques were detected by incorporation of [$^{125}$I]deoxycytidine (1 µC,i/ml) in the presence of 20 µg/ml of tetrahydrouridine. From 14 to 48 hr after infection.

V. Infection of susceptible cells or animals with vaccinia virus recombinants.

After identification of vaccinia virus recombinants, 2 or more successive plaque purifications were carried out to obtain pure recombinant virus. Susceptible cells such as BSC-1, HeLa, MRC-5, or others were infected to obtain large stocks of recombinant virus. The titers of the stocks were determined by serial dilution and plaque assay.

To express the foreign gene, cells were infected with 1 to 30 pfu/cell of crude or purified virus and incubations were carried out at 37° C. for up to 48 hr. The foreign gene product, depending on its nature was found in the cell culture medium or within the cells. When present in the cells, it was liberated by one of a number of methods including sonication, freeze-thawing, homogenization, or detergent treatment. The foreign protein was detected by immunological, enzymatic, and electrophoretic methods.

For infection of animals, recombinant virus was introduced intradermally, although other routes should be satisfactory. Formation of antibodies to the product of the foreign gene indicated that the foreign protein was made and was immunogenic.

EXAMPLES

In order to demonstrate the subject invention, we made several plasmids containing vaccinia virus promoters for insertion of foreign protein coding sequences to form chimeric genes. Protein coding sequences from other DNA viruses, RNA viruses and prokaryotes were inserted into the plasmids. Plasmids containing the chimeric genes then were used to transfect vaccinia virus infected cells and the recombinant virus was isolated by selective methods. Expression of the foreign genes was demonstrated in each case. Many routine procedures are described in detail in Maniatis, Fritsch, and Sambrook, *Molecular Cloning. A Laboratory Manual*, Cold Spring Harbor Laboratory (1982).

Example 1

Construction of plasmids pGS20 and pGS21 containing promoter from the 7.5K polypeptide gene (7.5K gene) of vaccinia virus, restriction endonuclease sites for insertion of foreign protein coding sequences, and an interrupted vaccinia virus thymidine kinase gene as flanking DNA.

(a) Isolation of 7,5K promoter DNA. A DNA fragment of approximately 275 bp that precedes and includes the RNA start site of an early vaccinia virus gene coding for a polypeptide known as 7.5K was obtained from a plasmid pAG4 [Yenkatesan et al., *Cell* 125:805–813 (1981)]. 70 μg of pAG4 was digested to completion with 100 units of restriction endonucleases HindII and RSaI (New England Biolabs) in 50 mM NaCl, 10 mM Tris-HCl (pH 7.4), 10 mM MgSO$_4$, and 1 mM dithiothreitol (DTT) (hereafter cell media salt restriction buffer) for 2 hr at 37° C. Resulting DNA fragments were separated by electrophoresis for 1 hr at 200 volts through a 1.5% agarose gel containing 40 mM Tris-Acatate (TriS-AC) (pH 8.0), 20 mM sodium acetate (NaAC), 2 mg EDTA, 18 mM NaCl. The gel was soaked in 1 μg/ml ethidium bromide (EtBr) containing agarose gel buffer for 10 min. DNA fragments within the gel were visualized under long wave ultraviolet light and a get strip containing a 275 by DNA fragment was excised using a razor blade. DNA within this gel strip was electroblotted onto a sheet of diethylaminoethyl (DEAE)-cellulose in 40 mM Tris-Ac (pH 7.2), 20 mM NaAc, 1 mM EDTA for 45 min. at 2.5 M and eluted from the DEAE-cellulose by shaking in 1.2M HaCl, 40 mM Tris-Ac (pH 7.2), 20 mM NaAc, 1 mM EDTA for 30 min at 25° C. DEAE-cellulose was removed by centrifugation at 12,000×g for 2 min, and DNA was precipitated from the supernatant by addition of 2 volumes of ethanol and recovered by centrifugation at 12,000×g for 5 min.

(b) Insertion of 7.5K gene promoter into plasmid pUC9, Two μg of pUC9 DNA was digested with 5 units of restriction endonuclease HindII in medium salt restriction buffer for 2 hr at 37° C. The mixture was heated to 70° C. for 5 min and DNA was extracted with an equal volume of phenol:chloroform (1:1) and recovered by ethanol precipitation. DNA was dephosphorylated at its 5' termini by incubation in 50 μl of 50 mM Tris-HCl (pH 9.0), 1 mM MgCl$_2$, 0.1 mM znCl$_2$, mM spermidine with 0.1 unit of calf-intestinal alkaline phosphatase (Boehringer Mannheim) for 30 min at 37° C. to prevent self-legation in the next step. The mixture was extracted twice with equal volumes of phenol:chloroform and DNA was recovered by ethanol precipitation, 0.5 μg of linearized, dephosphorylated pUC9 DNA was legated with 0.15 μg of the previously isolated vaccinia promoter DNA in 50 μl of 66 mM TrisHCl (pH 7.5), 6.6 mM NgCl$_2$; 10 mM DTT, 0.5 mM ATP together with 1 unit of T$_4$ DNA ligase at 12° C. for 15 hr. 25 μl of ligated DNA mixture was used to transform competent *E. coli* strain JM103 and 100 μl of transformed cell suspension was mixed with 50 μl of 2% X-gal and 10 μl of 0.1M IPTG and plated onto an L broth plate containing 1.5% bacto-agar (Difco) and 50 μg/ml ampicillin. The plate was incubated at 37° C. for 15 hr. White bacterial colonies were picked and grown in 10 ml of L broth containing 50 μg/ml ampicillin. Plasmid DNA was purified from 1.5 ml of bacterial cultures by the following procedure (hereafter referred to as minipreparation of plasmid DNA). Bacterial cells were pelleted by centrifugation (12,000×g, 1 min), resuspended in 0.1 ml of 25 mM Tris-HCl (pH 8.0), 10 mM EDTA, 50 mM glucose, 2 mg/ml lysozyme (lysis solution) and incubated at 4° C. for 30 min, 0.2 ml of 0.2 M NaOH, 1% sodium dodecyl sulfate (SDS) was added and the mixture incubated for a further 5 min on ice. 0.15 ml of 3M NaAc (pH 4.8) was added and the mixture incubated on ice for 1 hr followed by centrifugation at 12,000×g for 5 min. Plasmid DNA present in the supernatant was precipitated by addition of 1 ml ethanol, recovered by centrifugation and redissolved in 0.1 ml of 10 mM Tris-HCl (pH 7.5), 1 mM EDTA (TE buffer). Plasmid DNA preparations were screened for the presence of the vaccinia virus promoter by digestion of 10% of each plasmid preparation with restriction endonucleases HindIII and EcoRI (5 units of each enzyme in medium salt restriction buffer for 1 hr at 37° C.). DNA fragments were separated by agarose gel electrophoresis and visualized as described above. Plasmid preparations containing the vaccinia virus promoter were analyzed further to determine the orientation of the vaccinia promoter with respect to plasmid sequences. This was accomplished by digestion with restriction endonucleases HindIII and HincII or HincIII and EcoRI (5 units of each enzyme in medium salt restriction buffer at 37° C. for 1 hr) followed by agarose gel electrophoresis. A plasmid having with the vaccinia promoter reading toward the plasmid's unique BamHI restriction site was called pGS15. This plasmid was purified in large amounts by the following procedure, hereafter celled preparation of plasmid DNA. Bacteria containing the required plasmid were seeded into a 400 ml solution of M-9 medium containing 50 μg/ml ampicillin, 150 μml proline, 150 μg/ml leucine, 0.8 μg/ml vitamin B$_1$ and grown until the optical density at 590 nm reached 0.8. Chloramphenicol was added to a final concentration of 200 μl/ml and the culture was incubated for 12 hr at 37° C. Bacteria were pelleted by centrifugation (5.000×g. 10 min), washed in 10 mM Tris-HCl (pH 7.5), 0.15 M NaCl, resuspended in 10 ml lysis solution and incubated for 30 min on ice. 20 ml of 0.2 M NaOH, 0.1SDS were added and the incubation was continued for 5 min on ice, followed by addition of 15 ml of 3M NaAc (pH 4.8) and a further incubation on ice for 1 hr. The mixture was centrifuged (10,000×g, 10 min) and the supernatant was removed and recentrifuged (10,000×g, 10 min). Plasmid DNA was precipitated by addition of 2 volumes of ethanol and recovered by centrifugation at 10,000×g for 10 min. The DNA pellet was redissolved in 10 ml of TE buffer, the solution extracted twice with equal volumes of phenol:chloroform, the DNA recovered by ethanol precipitation and centrifugation and redissolved in 5 ml of TE buffer. 0.1 mg/ml of ribonuclease (pretreated by boiling for 10 min to inactivate deoxyribonucleases) was added and incubated for 30 min at 37° C. DNA was then precipitated by addition of NaAc (pH 7) to 0.1 M and 1.5 volumes of ethanol and recovered by centrifugation. Remaining RNA was removed from the DNA by dissolving the pellet in 0.3 M NaCl, 10 mM Tris-HCl (pH 7.5), 10 mM EDTA and filtering it through a Sephacryl-S300 column equilibrated in the same buffer. DNA eluting in the first $A_{260\ nm}$ peak was recovered by ethanol precipitation and centrifugation. DNA was finally dissolved in TE buffer, and stored at 4° C.

(c) Changing the HindIII site of pGS15 to an EcoRI site.

To enable the insertion of the vaccinia 7.5K gene promoter now cloned in pGS15 into the vaccinia thymidine kinase gene at the unique EcorRI site, it was necessary to change the HindIII site of pGS15 to in EcoRI site. This resulted in the vaccinia promoter and adjacent restriction sites being flanked by EcoRI sites, 20 µg of pGS15 DNA was cleaved with 50 units of HindIII restriction endonuclease in medium salt restriction buffer for 2 hr at 37° C. After extraction with phenol:chloroform, the DNA was recovered by ethanol precipitation and centrifugation. DMA termini were filled in to form blunt-ends by incubation of DNA in 0.2 mM dATP, 0.2 mM dCTP, 0.2 mM dGTP 0.2 mM dTTP, 0.5 mM DTT, 5 mM $MgCl_2$, 50 mM Tris-HCl (pH 7.8) with 2 units of DNA polymerase I large fragment (Boehringer Mannheim) at 37° C. for 45 min. DNA was recovered after phenol:chloroform extraction by ethanol precipitation and centrifugation. Synthetic EcoRI linkers were phosphorylated at their 5' termini by incubation with 1 unit of polynucleotide kinase in by 50 mM, 66 mM Tris-HCl (pH 7.6), 10 mM 2-mercaptoethanol at 37° C. for 30 min. the phosphorylated EcoRI linkers were then ligated onto linearized, blunt-ended pGS15 DNA by incubation at 4° C. for 15 hr in 0.5 mM ATP, 66 mM Tris-HCl 7.6), 6.6 mM $MgCl_2$, 10 mM DTT with one unit of T4 DNA ligase. DNA was then digested for 4 hr with 100 units of EcoRI in high salt restriction buffer [100 mM NaCl, 50 mM Tris-HCl (pH 7.5); 10 mM $MgSO_4$] and fragments were separated by agarose gel electrophoresis. A 290 bp fragment was purified by electroblotting onto DEAE-cellulose and ligated to pUC9 that had been cleaved with EcoRI and phosphatase treated. Transformation competent E. coli transformed by the ligated plasmid and transformants were selected and grown and the plasmid was amplified and purified as described above. The said plasmid was termed pGS19.

(d). Insertion of 7.5K gene promoter into vaccinia virus thymidine kinase gene. Plasmid pGS8 (derived from pBR328 by insertion of the vaccinia HindIII J fragment containing the vaccinia virus TX gene into the unique plasmid HindIII site and deletion of BamHI and EcoRI sites within the plasmid sequences), was grown and purified, 5 µg of pGS8 was digested with EcoRI and recovered after phenol:chloroform extraction and ethanol precipitation. 5' terminal phosphates were removed by treatment with alkaline phosphatase and the DNA was again recovered after phenol:chloroform extraction by ethanol precipitation, 0.5 µg of pGS8 DNA was then ligated together with 0.1 µg of the 290 bp DNA fragment containing the vaccinia virus promoter sequence flanked by EcoRI sites. This fragment had been excised from pGS19 by digestion with EcoRI and purified by agarose gel electrophoresis and electroblotting. Ligated DNA was used to transform competent E. coli cells strain HB101 and bacterial clones were screened for a plasmid containing the inserted vaccinia promoter sequence. Two such plasmids were amplified and purified; each contained the vaccinia promoter sequence but in opposite orientations with respect to plasmid sequences. The clones were termed pGS20 and pGS21. Both of these vectors have BamHI and SmaI restriction sites for insertion of foreign genes downstream from the translocated vaccinia 7.5K gene promoter and are flanked by vaccinia DNA sequences encoding segments of the thymidine kinase gene.

Example 2

Construction of plasmids pMM3 and pMM4 that contain the promoter of the vaccinia virus thymidine kinase gene, restriction endonuclease sites for insertion of foreign protein coding sequences, and flanking DNA including part of the thymidine kinase gene.

(a) Construction of pMM1. The recent mapping and sequencing of the vaccinia virus thymidine kinase (TK) gene (Weir et al., 1982; Weir and Moss, submitted for publication) allowed us to develop a strategy for isolating the TK promoter with its transcriptional initiation site but devoid of its translational start site. Inspection of the sequence showed a GTC between the transcriptional and translational start sites. If this sequence were ligated to GAC, a sequence GTCGAC recognized by several restriction enzymes would be created. This was achieved in the following manner. 25 µg of a plasmid derived from pUC9 by insertion of the vaccinia HindIII J fragment was cleaved with 50 units of ClaI (Boehringer Manheim) for 2 hr at 37° C. in 10 mM Tris-HCl (pH 8), 10 mM $MgCl_2$, 10 mM NaCl, giving a linear DNA molecule. The buffer composition was altered to 20 mM Tris HCl (pH 8.1), 100 mM NaCl, 12 mM $CaCl_2$. 1 µmM $HA_2EDTA$ and expected to have GTC between the TK gene transcriptional and translational starts at the opposing terminus. Upon ligation, these molecules would have a new SalI site (GTCGAC) generated. The mixture of molecules was ligated with 2 units of T4 DNA ligase (Boehringer Mannheim) at room temperature overnight in 20 mM Tris-HCl (pH 7.6), 10 mM DTT, 10 mM $MgCl_2$, 0.5 mM ATP. One µg of the ligated mixture was used to transform 100 µl of competent E. coli strain JM103 which were plated out on L-broth plates containing 50 µg/mM of ampicillin and grown at 37° C. overnight. 144 single colonies were transferred to a master agar plate containing ampicillin. The 144 colonies were arranged in 12 groups and each group was used to inoculate L-broth, ampicillin cultures. After overnight growth, minipreparations of plasmid were prepared and 2 µg of the purified DNAs were cleaved with 2 units of HindIII and 2 units of SalI for 2 hr at 37° C. in 10 mM Tris-HCl (pH 7.5), 10 mM $MgCl_{2,\ 100}$ mM NaCl. One DNA preparation contained a fragment of approximately 500 bp which would be the size of a fragment produced by HindIII and SalI if a SalI site had been generated after the TK transcriptional start site. The 12 colonies used to make this DNA preparation were grown singly in L-broth cultures and plasmid DNA purified and cleaved with HindIII and SalI. From one of the plasmids, a fragment of approximately 500 bp was detected by agarose gel electrophoresis. This fragment was recloned in phage M13mp8 and M13mp9 and the nucleotide sequence was determined for 100 nucleotides from both the HindIII and SalI sites according to the Sanger dideoxy chain termination method to prove that it had the desired sequences. The plasmid containing the HindIII-SalI fragment was designated pMM1 and was purified from a one liter culture of transformed E. coli.

(b) Construction of pMM2. 5 µg of a pUC9 derivative containing the vaccinia virus DNA HindIII J fragment was cleaved with 5 units of XhoI for 2 hr at 37° C. in 10 mM (Tris-HCl) pH 7.5, 10 mM MgCl$_2$. 150 mM NaCl (high salt restriction buffer). The buffer composition was adjusted to 40 mM dATP, dCTP, dGTP and dTTP, 250 mM NaCl, 75 MM Tris-HCl (pH 8.8). One unit of E. coli DNA polymerase I (large fragment) was added and the reaction incubated at room temperature for 1 hr in order to give blunt ends. Synthetic EcoRI linkers were phosphorylated at their 5 termini by incubation with polynucleotide kinase as described previously. Phosphorylated linkers were ligated at roam temperature to the blunt end DNA fragment as described previously. One mg of ligated mixture was used to transform E. coli JM103 and single ampicillin resistant colonies were picked and plasmids screened for a new EcoRI site where there had previously been an XhoI site. The plasmid with a new EcoRI site was designated pHH2.

(c). Construction of pMM3. By inserting the newly created EcoRI fragment that contains part of the TK gene from PMM2 into the EcoRI site of pMM1, anew plasmid was obtained that contains a number of restriction sites for insertion of a foreign gene coding sequence. 50 mg of pMM2 was cleaved with 75 units of EcoRI for 2 hr at 37° C. in high salt restriction buffer and the 1 kb EcoRI fragment was purified by agarose gel electrophoresis and electroblotting onto DEAE paper. Five mg of pMM1 was cleaved with 5 units of EcoRI for 2 hr at 37° C. as described previously, 1.5 units of bacterial alkaline phosphatase was added to the restriction digest and incubated for a further 30 min. The reaction mixture was then phenol extracted, chloroform extracted and ethanol precipitates, 0.25 mg of the EcoRI cleaved and alkaline phosphatase treated PMM1 was added to 0.5 mg of the isolated EcoRI fragment from pMM2 and the DNAs were ligated overnight. The ligated mixture was used to transform E. coli JM103 and plasmids were screened for a 1 kb EcoRI fragment inserted into pMM1 in the same orientation as present in the vaccinia genome. The resulting plasmid designated pMM3 contains unique HincII, AccI, SalI, BamHI and SmaI sites for insertion of genes next to the thymidine kinase promoter.

(d) Construction of pMM4. In order to have an EcoRI site to insert foreign genes under control of the TK promoter, it was first necessary to remove the second EcoRI site distal to the TK promoter. This was achieved in the following manner, 100 mg of pMM2 was partially cleaved with 20 units of EcoRI for 15 min at 37° C. in high salt restriction buffer and the linear DNA molecule formed by cleavage at a single EcoRI site was isolated by agarose gel electrophoresis and electroblotted onto DEAE paper, 250 mg of the linear DNA molecule was incubated with 0.5 units of E. coli DNA polymerase I (large fragment) at 15° C. for 1 hr in 40 ml dATP, dCTP, dGTP, dTTP, 250 mM NaCl, 75 mM Tris-HCl (pH 8.8). The reaction mixture was then phenol extracted, chloroform extracted and ethanol precipitated. After ligation, the plasmid was used to transform E. coli JM103. The resulting transformed E. coli were screened for the presence of a plasmid with the EcoRI site farthest from the promoter deleted. The plasmid, designated pMM4, contains unique HincII, AccI, SalI, BamHI, SmaI, and EcoRI sites for insertion of foreign genes, Example 3.

Formation of vaccinia virus recombinants that express the prokaryotic chloramphenicol acetyltransferase (CAT) gene.

(a) insertion of the CAT gene into pGS21. A 770 bp DNA fragment containing the CAT gene was isolated from pBR328 by cleavage of pBR328 DNA with restriction endonuclease TaqI followed by agarose gel electrophoresis, electroblotting onto DEAE-cellulose, elution and recovery of DNA by ethanol precipitation and centrifugation. This 770 bp DNA fragment was inserted into plasmid pUC7 as follows. pUC7 DNA was cleaved with restriction enzyme AccI, the 5' terminal phosphates were removed with calf intestinal alkaline phosphatase and the DNA was recovered after phenol:chloroform extraction by ethanol precipitation, 0.5 μg of linearized dephosphorylated plasmid DNA was ligated with 0.2 μg of the 770 bp fragment under standard conditions described above. Ligated DNA was then used to transform E. coli strain JM103 and white bacterial colonies that grew on 1.5% bacto-agar plates containing L-broth, 50 μg/ml of ampicillin, X-gal and IPTG, were picked and grown in L-broth, Mini-preparation of plasmid DNA were screened for the presence of the 770 bp DNA of fragment containing the CAT gene by digestion with BamHI and agarose gel electrophoresis. Such a plasmid was grown, amplified and purified by standard procedures as described above and called pGS29.

Plasmid pUC7 contains 2 BamHI sites closely flanking the AccI sites. Consequently after insertion of the CAT gene into the AccI site, this gene was, now excisable as a 780 bp fragment by BamHI. After BamHI digestion of pGS29, the 780 bp fragment was isolated by agarose gel electrophoresis, electroblotted onto DEAE-cellulose, eluted and recovered by ethanol precipitation.

The next step was the insertion of this BamHI DNA fragment into plasmid vector pGS21. pGS21 DNA was linearized by cleavage with BamHI, the 5' terminal phosphates were removed by digestion with calf intestinal alkaline phosphatase and DNA was recovered by phenol:chlorofom extraction and ethanol precipitation, 0.5 μg of linearized, dephosphorylated pGS27 DMA was ligated with 0.2 μg of the 780 by DNA fragment under standard conditions one the ligated DNA was then used to transform, competent E. coli cells strain HB101. Transformed cells were plated onto an L-broth plate containing 1.5% bacto-agar and 50 μg/ml ampicillin After incubation for 15 hr at 17° C, bacterial colonies were picked grown in L-broth containing 50 μg/ml ampicillin and plasmid DNA was purified by the minipreparation procedure. Plasmid DNA was screened for the presence of the 780 bp CAT gene BamHI fragment in the correct orientation with respect to the vaccinia promoter by digestion with BamHI or EcoRI followed by agarose gal electrophoresis. Such a clone was called pGS24 and was grown, amplified and purified as described above.

(b) Insertion of the chimeric CAT gene into vaccinia virus. A 25 sq cm monolayer of TK⁻143 cells was infected with wild type vaccinia virus at 0.01 pfu/cell. A mixture of 1 μg of pGS24, 1 μg vaccinia virus DNA, and 20 μg of calf thymus DNA was precipitated with 125 mM CaCl; The fine suspension was used to transfect the cells at 2 hr after infection. After 30 min at 25° C., 7.2 ml of Eagle medium containing 8% fetal bovine serum was added and the monolayer was incubated for 3.5 he at 37° C. The culture medium was then removed and replaced by 8 mi fresh Eagle medium containing 8% fetal bovine serum and the incubation was continued at 37° C. for two days. Cells were scraped from the bottles, pelleted by centrifugation (2,000×g, 5 min) and resuspended in 0.5 ml of Eagle medium containing bovine serum.

(c) Selection of recombinant vaccinia virus containing the chimeric CAT gene. Thymidine kinase negative vaccinia virus recombinants were selected by plaque assay in TK⁻143 cells with a 1% low melting agarose overlay containing 25 μg/ml BUdR. After three days at 37° C., cell monolayers were stained with 0.005% neutral red, plaques were picked using a sterile Pasteur pipette and placed in 0.5 ml of Eagle medium containing 2.5% fetal bovine serum. After freezing and thawing 3 times and sanitation, 0.25 ml of each plaque was used to infect 16 mm diameter monolayers of TK⁻143 cells. Two hr after infection, culture medium was removed and monolayers were overlayed with 1 ml of Eagle medium containing 2.5% fetal bovine serum and 25 $\mu$g/ml BUdR. After two days incubation at 37° C., cell monolayers were scraped from wells, pelleted by centrifugation, resuspended in 0.5 ml of 0.15 M NaCl, :10 mM Tris-HCl (pH 7.5), frozen and thawed 3 times and 0.1 ml was transferred to nitrocellulose using a micro filtration manifold (Schleichsr and Schuell). After procedures to denature, neutralize end fix DNA to the nitrocellulose, the filter was hybridized with $^{32}$p-labeled CAT gene DNA. After washing the filter, an autoradiograph was obtained. Virus recombinants showing positive hybridization to zip-$^{32}$P-CAT DNA were further plaque purified in 7K 143 cells with BUdR selection and the screening procedure for CAT DNA repeated. A clone positive for CAT DNA at this stage was then amplified once in TK cells with BUdR selection, once in CV-1 cells without selection and the virus titre determined by plaque assay in CV-1 cells. This virus was called JCAT 24.

(d) Analysis of expression of chimeric CAT gene. CV-1 cells were Infected with vCAT24 at 10 pfu/cell. After 24 hr at 37° C, cells were scraped, pelleted, resuspended in 0.2 ml of 0.25M Tris-HCl (pH 7.8) and sonicated. Cell debris was removed by centrifugation (12,000×g, 5 min) and the supernatant was assayed for chloramphenicol acetyltransferase activity essentially as described by Gorman et al., *Mol. Cell Biol*, 2:1044–1051 (1982). Extracts from cells infected with vCAT24 contained an enzyme activity that acetylated chloramphenicol as demonstrated by thin layer chromatography. Extracts from both uninfected and wild-type vaccinia virus infected cells contained no detectable chloramphenicol acetyltransferase activity.

Example 4.

Construction of vaccinia virus expressing chimeric herpes thymidine kinase (HTK) gene, 50 $\mu$g of a plasmid containing a BamHI fragment including the HTK gene [Enquist et al., *Gene* 7:335–342 (1979)] was cleaved with 50 units of HincII and 50 units of PvuII for 2 hr at 37° C. in medium salt restriction buffer. A 8 kb HincII-PvuII fragment devoid of the HTK transcriptional start site but containing all of its coding sequence was isolated by agarose gel electrophoresis and electroblotted onto DEAE paper. Five $\mu$g of pUC7 was cleaved with 5 units of HincII for 2 hr at 37° C. in medium salt restriction buffer. 1.5 units of calf intestinal alkaline phosphatase was added and the reaction mixture was incubated for a further 30 min after which it was phenol extracted, chloroform extracted and ethanol precipitated, 250 mg of this DNA was ligated, with 500 mg no of the isolated HincII-PvuII HTK fragment and *E. coli* JM103 cells were transformed with the ligated mixture. Plasmids were isolated from the transformed bacteria and screened for the HincII- PvuII fragment inserted into pUC7. This plasmid was designated pVH4 . 50 $\mu$g of pVH4 was cleaved with EcoRI and the EcoRI fragment containing the HTK gene was isolated by agarose gel electrophoresis and electroblotted onto DEAE paper. Five $\mu$g of pMM4 was cleaved with EcoRI; 1.5 units of calf intestinal alkaline phosphatase was added and the reaction incubated for a further 30 min. The reaction mixture was then phenol extracted, chloroform extracted and ethanol precipitated. 250 mg of this cleaved plasmid was ligated to 500 mg of the EcoRI fragment containing the HTK coding sequences and this ligated mixture was used to transform *E. coli* JM103. Single ampicillin resistant colonies were screened for a plasmid containing HTK coding sequences at the EcoRI site of pMM4. This recombinant plasmid was designated pMM20 and combines the vaccinia virus TK transcriptional regulatory sequences with an uninterrupted Herpes TK coding sequences, and the distal half of the vaccinia virus TK gene. This chimeric gene is flanked with vaccinia sequences such that homologous recombination would occur at the site of the vaccinia virus TK gene of wild type virus.

Human TK⁻143 cells were infected with 0.01 pfu/cell of a vaccinia virus TK⁻ mutant Bajszar et al., *J. Viral.*, in press). The TK lesion maps between the vaccinia TK transcriptional start site and the EcoRI site in the vaccinia TK gene and hence the lesion could not be restored to wild type vaccinia TK by recombination with pMM20. One jig of calcium phosphate precipitated (pH 20 DNA was introduced by transfection into TK⁻143 cells infected with TK 13 vaccinia virus. Selection procedures described earlier for selection of TK⁺, virus were used. Isolated single TK⁺ plaques were plaque purified again and checked for synthesis of the herpesvirus TK. Since [I$^{125}$]dC is a specific substrate for the herpesvirus TK, but not for vaccinia virus or cellular TK, [$^{125}$]dc is incorporated into viral DNA only if herpes virus TK is expressed. Autoradiography of cell monolayers, infected with the putative recombinant virus, in the presence of [$^{125}$]dC revealed dark spots on the film corresponding to viral plaques showing that the TK⁺ virus was expressing herpesvirus TK. That the herpes TK was integrated into the viral genome was shown by DNA—DNA hybridization of $^{32}$P-labeled HTK DNA to blots of separated restriction digests of purified recombinant viral DNA. A further confirmation that herpesvirus TK was expressed was obtained by plaquing a recombinant virus stock in the presence and absence of 40 $\mu$g/ml bromodeoxycytidine (BCoR). Wild type vaccinia virus plaques were slightly reduced in size but the number of plaques remained constant when the media was supplemented with 40 $\mu$g/ml BUR. However, the titer of recombinant virus was reduced between 10 to 100-fold in the presence of 40 $\mu$g/ml 8CdR, as expected if synthesis of the herpesvirus TK had occurred.

Example 5.

Construction of vaccinia virus recombinants expressing chimeric vesicular stomatitis virus (VSV) N gene, 50 $\mu$g of pJS223 (a plasmid containing a cDNA copy of VSV N gene, Sprague et al., in press) was cleaved with 50 units of XhoI for 2 hr at 37° C. in high salt restriction buffer. The smaller fragment containing N gene DNA was isolated by agarose gel electrophoresis and electroblotting onto DEAE paper. Five $\mu$g of pMM3 was cleaved with 5 units of SalI for 2 hr at 37° C. 1.5 units of calf intestinal alkaline phosphatase was added for a further 30 min. The reaction mixture was phenol extracted, chloroform extracted, and ethanol precipitated, 250 mg of this DNA was ligated to 500 mg of the isolated XhoI fragment and *E. coli* JM103 were transformed with the ligated mixture. Single ampicillin resistant colonies were screened for the presence of VSV cDNA cloned into pMM3. The chimeric plasmid containing the vaccinia promoter contiguous with the VSV cDNA was designated pMM17. Cells were infected with wild type vaccinia virus and transfected with this plasmid. After 46 hr, the cells were disrupted and TK⁻ virus was selected by plaque formation with BUdR in the agar overlay. Expression of the chimeric VSV N gene was shown by standard immunoprecipitation methods. Recombinant virus was used to infect cells at 20 pfu/cell and [$^{35}$S]methionine was added to the medium. At 6 hr after infection, a cytoplasmic extract was made from the infected cells. Rabbit anti-VSV antiserum and staph A protein were used to precipitate VSV proteins. After dissociation of the Staph A -protein complex, the proteins were analyzed on a 10% polyacrylamide gel in parallel with authentic VSV labeled proteins. After fluorography, a protein that was immunoprecipitated from cells infected with the recombinant virus was seen to comigrate with authentic VSV N protein. This result demonstrated that the vaccinia virus recombinant expressed the chimeric VSV N gene.

Example 6.

A 1,350 bp DNA fragment containing the HBsAg gene was obtained from a plasmid [Moriarity et al., *Proc. Natl. Acad. Sci. U.S.A.* 78:2606–2670 (1981)). Nucleotide sequence data suggested that the first ATG codon after one of the BamHI restriction endonuclease sites represented the initial methionine residue of HBsAg. The fragment containing the HBsAg gene was isolated from 50 μg of this plasmid by digestion with 100 units of BamHI in 50 mM NaCl, 10 mM Tris-HCl (pH 7.5), 10 mM $MgS0_4$, 10 mM dithiothreitol (DTT) (hereafter cell medium restriction buffer) for 2 hr at 37° C. DNA fragments were separated by electrophoresis at 200 volts for 1 hr through a 1% agarose gel containing 40 mM Tris-acetate (Ac) (pH 8.0), 20 mM NaAc, 2 mM EDTA, 18 mM NaCl. The gel was soaked in 1 g/ml ethidium bromide (EtBr) and DNA fragments were visualized by illumination with long wave ultraviolet light. A gel strip containing a DNA fragment of 1.35 kilobase pairs (kb) was excised from the agarose gel and DNA within this, strip was transferred to diethylaminoethyl (DEAE)-cellulose by electroblotting in 40 mM Tris-Ac (pH 7.2), 20 mM NaAc, 1 EDTA for 1 hr at 2.5 mA. DNA was eluted from the DEAE-cellulose paper by shaking in 1.2 M NaCl, 40 mM Tris-Ac (pH 7.2), 20 nM NaAc, 1 mM EDTA for 30 min at 25° C. and recovered from the supernatant by addition of 2 volumes of ethanol followed by centrifugation at 12,000×g for 5 min.

The plasmids pGS20, pGS21, and pMM3 were linearized by digestion with 2 units of BamHI/μg DNA in medium salt restriction buffer for 2 hr at 37° C. The linearized plasmids were then dephosphorylated at their 5' termini by incubation with 0.1 unit of calf intestinal alkaline phosphatase in 50 mm iris-HCl (pH 9.0), 1 mM $MgCl_2$, 0.1 mM $ZnCl_2$, 1 mM spermidine for 30 min at 37° C. After two extractions with equal volumes of phenol:chloroform (1:1), the DNA was recovered by ethanol precipitation and centrifugation, 0.5 μg of each linearized, dephosphorylated plasmid was ligated with 0.2 μg of the 1.35 kb BamHI fragment containing the HBsAg gene in 66 mM Tris-HCl (pH 7.5), 6.6 mM $MgCl_2$, 10 mM DTT, 0.5 mM ATP for 15 hr at 12° C. Ligated DNA was used to transform competent *E. coli* cells strain HB101 and the transformed cells were grown for 15 hr at 37° C. on L-broth plates containing 1.5% bacto-agar and 50 μg/ml ampicillin. Bacterial colonies were picked and grow in 10 ml of L-broth containing 50 μg/ml of ampicillin for 15 hr at 37° C. Plasmid DNA was prepared from 1.5 ml of bacterial cultures by the following mint-preparation of plasmid DNA. Bacterial cells were pelleted by centrifugation (12,000×g, 1 min) and resuspended in 0.1 ml of lysis solution 125 mM Tris-HCl (pH 8.0), 10 mM EDTA, 50 and glucose, 2 μg/ml lysozyme] and incubated an ice for 30 min. 0.2 ml of 0.2 M NaOH, 1% sodium dodecyl sulfate (SDS) was added and the mixture incubated on ice for 5 min. 0.15 ml of 3H NaAc (pH 4.8) was added and after a further 1 hr incubation on ice, the mixture was centrifuged at 12,000×g for 5 min. Plasmid DNA was precipitated from the supernatant by addition of 1 ml of ethanol, recovered by centrifugation (12,000×g, 5 min) and finally redissolved in 0.1 ml of 10 mM Tris-HCl (pH 8.0) 1 mM EDTA (TE buffer).

Plasmid DNAs were screened for the presence of the 1.35 kb BamHI fragment containing the HBsAg gene by digestion of 10% of each plasmid DNA sample with 5 units of restriction eadonuclease BamHI in medium salt restriction buffer for 1 hr at 37° C., followed by agarose gel electrophoresis and EtBr staining.

Since the 1.35 kb BamHI hepatitis B virus DNA fragment could be inserted in either of two orientations within each of the plasmids, additional screening was necessary. Plasmids derived from pGS20 and pGS21 were digested with XbaI restriction endonuclease in 100 mM NaCl, 50 mM Tris-HCl (pH 7.5), 10 MM $MgSO_4$ (high salt restriction buffer) for 1 hr at 37° C. and analyzed by agarose gel electrophoresis. The identification of XbaI fragments of approximately 830 or 1,730 bp discriminated between derivatives of pGS20 that contained the HBsAg gene in incorrect and correct orientation, respectively. XbaI fragments of 2,150 bp or 1,150 bp discriminated between derivatives of pGS21 that had the HBsAg gene in incorrect and correct orientations, respectively. Plasmids from pMM3 were screened by HincII digestion in medium salt restriction buffer followed by agarose gel electrophoresis. The presence of the HBsAg gene in correct orientation was indicated by generation of fragments of approximately 5,400 by and 200 by whereas fragments of 4,400 bp and 1,200 bp resulted when HBsAg was in the incorrect orientation. Plasmids were then grown, amplified and purified as follows. Transformed bacteria were seeded into 400 ml cultures of M-9 medium containing 150 μg/ml leucine, 150 μg/ml proline, 0.8 μg/ml vitamin. $B_1$, 50 μg/ml ampicillin and grown at 37° C. until the culture reached an optical density of 0.8 at 590 nm. Chloramphenicol was then added to a concentration of 200 μg/ml and the culture was incubated for 12 hr at 37° C. Bacteria were pelleted by centrifugation (5,000×g, 10 min), washed once in 0.15 M NaCl, 10 mM Tris-HCl (pH 7.5) and then resuspended in 10 ml of lysis solution (above). After incubation for 30 min on ice, 20 ml of 0.2 M NaOH, 1% SDS was added and incubation continued for 5 min, 15 al of 3 M NaAc (pH 4.8) was than added and after incubation on ice for a further 1 hr, the mixture was centrifuged at 10,000×g for 10 min. The supernatant was recentrifuged at 10,000×g for 10 min and plasmid DNA was precipitated from the final supernatant by addition of 2 volumes of ethanol. After centrifugation at 10,000×g for 5 min, the pellet was redissolved in 10 ml of TE buffer and the solution was extracted twice with equal volumes of phenol:chloroform. DNA was recovered by ethanol precipitation and centrifugation and redissolved in 5 ml of TE buffer. 0.1 mg/ml of ribonuclease (heated at 100° C. to inactivate contaminating deoxyribonucleases) was added and the mixture was incubated for 30 min at 37° C. DNA was then precipitated by addition of NaAc (pH 7) to 0.1M and 1.5 volumes of ethanol and was recovered by centrifugation at 5,000×g for 5 min. Remaining RNA was removed from the DNA by dissolving the pellet in 0.3 M NaCl, 10 mM Tris-HCl (pH 7.5), 10 mM EDTA and passage through a sephacryl-S300 column equilibrated with the same buffer. DNA eluting in the first peak was recovered by ethanol precipitation and centrifugation, dissolved in 1.0 ml of TE buffer and stored a 4° C. Plasmids from pGS21 that have the HBsAg gene in incorrect and correct orientations relative to the translocated promoter have been designated pHBs1 and pHBs2, respectively. Plasmids from pGS20 that have the HBsAg gene in incorrect and correct orientations have been designated pHBs3 and pHBs4. The plasmid from pMM3 that has the HBsAg gene in correct orientation relative to the TK promoter has been designated pHBs5.

Example 7.

Formation of vaccinia virus recombinants containing a chimeric HBsAg gene. Plasmids containing a chimeric HBsAg gene flanked by segments of the vaccinia virus TK gene were used to transfect cells infected with wild-type thymidine kinase positive (TK$^+$) vaccinia virus. Confluent monolayers of CV-1 mM MRC-5 cells (25 sq cm) were infected with vaccinia virus at 0.01 plaque forming units (pfu) per cell. One μg of the plasmid, 1 μg of vaccinia virus DNA and 20 μg of calf thymus DNA were mixed in 1 ml of 0.1% dextrose, 0.14 M NaCl, 5 mM KCl, 1 mM $Na2HPO_4$, 20 mM Hepes and precipitated by addition of $CaCl_2$ to a final concentration of 0.125 M. The mixture was agitated gently for 45 min at 250° C. and 0.8 ml of the fine suspension was added at 2 hr after infection to a monolayer from which medium had been removed. After 30 min at 25° C., 7.2 ml of Eagle medium containing 8% fetal bovine serum (FSS) was added and the incubation was continued at 37° C. for a further 3.5 hr. At 6 hr after infection, the medium was replaced with fresh medium containing 8% FBS and the incubation was continued for 2 days. Cells were then scraped from the bottle, pelleted, resuspended in 0.5 ml of tissue culture medium and homogenized to break cells and liberate the virus.

Only a small percentage of the virus produced in transfected cells was recombinant. These recombinants were isolated by selective and non-selective methods. Selection was possible because the HBsAg coding sequences were inserted into the TK gene and interrupted its function. Because of the thymidine kinase negative (Tel phenotype, recombinant virus was able to form plaques in the presence of 5-bromodeoxyuridine (BUdR) whereas the origins $TK^+$ virus did not. Non-selective procedures were carried out as described by Villarreal and Berg [Science 196:183–185 (1997)].

Monolayers of $TK^-$143 cells were inoculated with virus from transfected cells and 2 hr later were overlayed with medium containing 1% low melting agarose , 25 μg/ml BUdR, add 2.5% FBS. After 3 days at 37° C. in a humidified 5% $CO_2$ atmosphere, the cells were stained with 0.0.005% neutral red. Greater than 50% of the plaques visualized under these conditions were shown by dot blot hybridization to contain recombinants with hepatitis B virus DNA. For the latter procedure, individual virus plaques were picked using a sterile Pasteur pipette and used to infect $TK^-$143 cell monolayer in 16 mm diameter multiwell dishes. After 48 hr of incubation in medium containing BUdR at 37° C., the cells were scraped, lysed by three freeze-thaw cycles, and collected on nitrocellulose sheets by filtration through a micro-sample manifold (Schleicher and Schuell, N H). The filter was washed with 100 mM NaCl, 50 mM Tris-HCl, –pH 7.5), blotted 3 times on successive Whatman 3 MM filter papers saturated with (1) 0.5 M NaOH, (2) 1 M Tris-HCl (pH 7.5), and (3) 2×SSC (SSC is 0.15 M NaCl, 0.015 M sodium citrate), baked at 80° C. for 2 hr and then incubated with 5×Denhardt's solution [Denhardt, Biochem. Biophys. Res. Commun. 23:641–646 (1966)] supplemented with 0.1 mg/ml of denatured, sheared saloon sperm DNA in 4×SSC at 65° C. for 4 hr. Hepatitis B virus DNA, labeled with $^{32}p$ by nick translation [Rigby et al., *J. Mol. Biol*, 113: 237 (1975)], and sodium dodecyl sulfate (SDS) at a final concentration of 0.1% were added and hybridization continued for 15 hr at 65° C. The filter was washed twice for 15 min at 65° C. with 2×SSC/0.1% SDS and then with 0.2×SSC/0.15 SDS. An autoradiograph was made by placing the filter next to X-ray film and the presence of dark spots on developed film identified recombinant virus containing the HBsAg gene. Recombinant virus, was plaque purified a second time in TR-143 cells with an agar overlay containing 25 μg/ml of BUdR and recombinant virus stocks were then prepared. The recombinant virus stocks were designated $vHBs_1$l, $vHBs_2$, $vHBs_3$, $vHBs_4$ and $vHBs_5$ to correspond with the names given to the plasmids from which they were derived.

Example 8.

Expression of HBsAg in cells infected with vaccinia virus recombinants. Evidence for HBsAG expression in cells infected with vaccinia virus recombinants was obtained by a standard radioimmunoassay procedure (AUSTRIA, Abbot Laboratories). Monolayers of CV-1 cells were infected with 10 plaque forming units (pfu) per cell of vaccinia virus recombinants, wild-type vaccinia virus, or mock infected as indicated in Table 1. Two hr after infection, the virus inoculum was removed and cells were overlayed with Eagles medium containing 2.5% FBS. After incubation for 24 hr, the cells were scraped from culture flasks and separated from culture medium by centrifugation (2,000×g, 5 min). Cell pellets were resuspended in 3.5 ml of TBS [Q.15 M NaCl, 10 mM Tris-HCl (pH 7.5)], frozen and thawed 3 times, sonicated and centrifuged .(12,000×g, 1 min) to remove debris. The supernatant and tissue culture medium were assayed for HBsAg by radioimmunoassay. Beads coated with anti-HBsAg antibody were incubated with 0.2 ml of sample for 2 hr at 45° C., thoroughly rinsed 8 times with 1 ml $H_2O$ and then reincubated with $^{125}I$-labeled antibody against HBsAg for 1 hr at 45° C. Beads were washed again and then counted in a gamma-ray scintillation counter. The quantity of HBsAg present was calculated by reference to positive and negative controls supplied by Abbot Laboratories and incubated in parallel.

As shown in Table 1, HBsAg was produced in greatest amount by cells infected with vHBs2 and vHBs4. Lesser amounts of HBsAg were made in cells infected with vHBs5. By contrast, those recombinants that did not have the HBsAg gene in correct orientation with the translocated vaccinia virus promoter, vHBs1 and vHBs3, made barely detectable levels of HBsAg. Significantly, much of the HBsAg was excreted into the culture medium. Release of HBsAg was not due to cell lysis since 90% of infectious virus remained cell associated. Table 1 also shows that the similar yields of virus were obtained after infection with wild-type (WT) or recombinant virus.

The nature of the HBsAg synthesised by cells infected with vaccinia virus recombinants was analyzed by immunoprecipitation. Monolayers of CV-1 cells infected with purified vaccinia virus recombinants at 30 pfu/cell were incubated in Eagles medium containing 0.01 mM methionine for 4 hr after infection. The cells were then incubated for 20 min at 37° C. with fresh Eagles medium without methionine supplemented with [$^{33}$S]methionine (120 $\mu Ci/5\times10^6$ cells). Excess [$^{35}$S]methionine was removed by washing the cells 3 times with ice-cold phosphate buffered saline and cell extracts were prepared by incubation of cells in 0.5 ml of 0.1% aprotinin, 0.1 H Tris-HCl (pH 8.0), 0.1 M NaCl, 0.5% NP40, for 10 min. on ice, followed by centrifugation. 80% of the supernatant was incubated with 25 $\mu$l of guinea pig non-immune serum at 4° C. for 15 hr and immune complexes were removed by addition of 50 $\mu$l of a formalin-treated staphylococcal A suspension and incubation for 30 min at 4° C., followed by centrifugation. 20 $\mu$l of guinea pig HBsAg antiserum was then added, incubated for 15 hr at 4° C. and then immune complexes were removed by addition of staphylococcal A suspension as above, followed by centrifugation. The pellet was washed twice in 0.05 M Tris-HCl (pH 7.5), 0.15 M NaCl, 0.1% SDS, 1% Triton X-100, 1% sodium deoxycholate and twice in 0.4 M LiCl, 2 M urea, 10 mM Tris-HCl (pH 8.0). Immune complexes were eluted from the staphylococcal A pellet by incubation in 50 $\mu$l of 0.06 M Tris-HCl (pH 6.8), 3% SDS, beta mercaptoethanol, 10% glycerol, 0.002% bromophenol blue for 15 min at 25° C. After centrifugation, the supernatant was boiled and electrophoresed through a 15% polyacrylamide gel. The gel was fixed, treated with Enhance (New England Nuclear Corporation) and a fluorograph was obtained. Examination of the fluorograph indicated that two polypeptides were specifically immunoprecipitated. These had molecular weights of 23,000 and 25,400 and comigrated on polyacrylamide gels with polypeptides immunoprecipitated by HBsAg antiserum from a hepatoma cell line PLC/PRF/5. The nature of the HBsAg excreted from cells infected with vaccinia virus recombinants was further examined. Tissue culture medium, harvested 24 hr after infection of CV-1 cells with 30 pfu/cell of vaccinia virus recombinant vHBs4, was clarified by centrifugation at 2,000×g for 5 min and then recentrifuged at 75,000×g for 24 hr at 4° C. The pellet was resuspended in 4.5 ml of 10 mM Tris-HCl (pH 7.5), 150 mM NaCl, 1 mM EDTA and then 1.38 grams of CsCl was added to a final density of 1.2 g/cm$^3$. The sample was centrifuged at 220,000×g for 64 hr at -4° C. and gradient fractions were collected. Diluted samples were tested for HBsAg by radioimmunoassay. A peak of HBsAg was detected at a density of 1.2 g/cm$^3$ which was identical to a peak of HBsAg obtained when culture medium from hepatoma cell line PLC/PRF/5 was treated in parallel. The peak fractions of HBsAg were dialyzed against phosphate buffered saline (PBS) and recentrifuged on a 5 to 30% (w,w) sucrose gradient in PBS for 4.5 hr at 150,000×g at 4° C. Gradient fractions were collected and samples were diluted and assayed for HBsAg by radioimmunoassay. A peak of HBsAg was detected which sedimented at the same rate as the HBsAg from hepatoma cell line PLC/PRF/5. When samples from these peaks were analyzed by electron microscopy, particles of HBsAg were detected.

In all respects examined (including antigenicity, polypeptide composition, buoyant density, sedimentation rate), the HBsAg excreted from cells infected with vaccinia virus recombinant vHBs4 was indistinguishable from HBsAg particles released from hepatoma cell line PLC/PRF/5.

TABLE 1

Production of HBsAg and Vaccinia Virus from Infected Cells

|  | ng HBsAg/5 × 10$^6$ cells | | Virus yield (pfu) | |
| --- | --- | --- | --- | --- |
|  | cell extract | culture medium | cell extract | culture medium |
| Uninfected | <1 | <1 | ND | ND |
| WT | <1 | <1 | 7.8 × 10$^8$ | 7.7 × 10$^7$ |
| vHBs1 | 11 | 20 | 8.3 × 10$^8$ | 10.2 × 10$^7$ |
| vHBs2 | 835 | 1700 | 7.9 × 10$^8$ | 9.9 × 10$^7$ |
| vHBs3 | 14 | 25 | 9.1 × 10$^8$ | 9.0 × 10$^7$ |
| vHBs4 | 930 | 1700 | 8.8 × 10$^8$ | 9.8 × 10$^7$ |
| vHBs5 | 35 | 80 | 10.3 × 10$^8$ | 9.6 × 10$^7$ |
| Hepatoma cells | 340 | 900 | ND | ND |

CV-1 cell monolayers were infected with purified wild-type (WT) or vaccinia virus recombinants (vHBs 1–5) at 30 plaque forming units (pfu)/cell or mock infected. At 2 hr, virus inoculum was replaced with 2.5 ml of Eagle medium containing 2.5% fetal bovine serum. Cells were harvested at 24 hr and separated from culture medium by centrifugation at 2,000×g for 5 min. Cell pellets were suspended in 2.5 ml of phosphate buffered saline, frozen and thawed 3 times and sonicated. Equal portions of cell extracts and culture medium were tested for HBsAg by radioimmunoassay and for vaccinia virus by plaque assay in CV-1 cells. Culture medium and a cell extract prepared as above from a hepatoma cell line PLC/PRF/5 three days after confluency were tested in parallel for HBsAg.

Example 4.

Vaccinia virus (strain WR) was obtained from American Type Culture Collection, grown in HeLa cells and purified from cytoplasmic extracts by sucrose gradient centrifugation. Influenza virus A/Jap/305/57 (H2N2) is grown in 10-day-old chick embryos.

Polypeptide analysis.

CV-1 monolayers are infected with 30 plaque forming units per cell of vaccinia virus or similar amounts of influenza virus. From 2 to 6 hours after infection, approximately 31×10$^6$ cells are labeled with 80 $\mu$Ci of [$^{35}$S]-methionine (1,000 Ci/mmole) in medium otherwise lacking this amino acid. Cells are lysed with 0.5% Nonidet P40 and incubated with goat pre-immune serum followed by formalin treated staphylococcal cells. After centrifugation, the supernatant is incubated with goat anti-influenza virus A/Jap/305/57 serum followed by staphylococcal cells. Immunoprecipitated polypeptides are resolved by electrophoresis through a 15% polyacrylamide gel and detected by autoradiography.

The construction of a chimeric gene containing the transcriptional regulatory signals and RNA start site of an early vaccinia virus gene and the translation start site and coding sequences of the influenza HA gene is diagrammed in FIG. 1. The starting plasmids are pJHB16, which contains a 1.7 kb segment of the HA gene of influenza virus A/Jap/305/57, and pGS20, which contains a 265 bp segment including the transcriptional regulatory signals and RNA start site of an early vaccinia virus gene translocated within the body of the TK gene. In pJHB16, a synthetic HindIII linker precedes the first nucleotide of the HA translation initiation codon and a BamHI at the distal end of the gene. The HindIII site of pJHB16 was changed to a BamHI site so that the HA segment could be cloned into the unique BamHI site of pGS20. The resulting plasmid, pGS36, contains the HA gene correctly oriented with respect to the vaccinia promoter. The plasmid is then used to transfect CV-1 cell infected with wild-type vaccinia virus. Homologous recombination between vaccinia TK sequences in the plasmid and virus genome resulted in insertion of the HA gene into vaccinia virus. The virus progency is then plaque assayed on TK⁻ cells in the presence of BUdR to select Tk⁻ recombinants. The latter are distinguished from spontaneous TK⁻ mutants by dot blot hybridization to $^{32}$P-labeled influenza virus HA DNA. After two plaque purifications, recombinant virus stocks derived from pGS36 are labeled vInf1.

Analysis of recombinant virus DNA.

DNA was extracted from purified virus particles, digested with appropriate restriction endonucleases, and separated by agarose gel electrophoresis. DNA fragments were transferred to duplicate nitrocellulose sheets by bidirectional blotting and hybridized to $^{32}$P-labeled DNA from the TK containing HindIII J fragment of vaccinia virus or the HA gene of influenza virus. Autoradiographs of HindIII digests demonstrate that the 5 kB HindIII J fragment of wild-type vaccinia virus is replaced by a 7 kb fragment in vInf1. This kb fragment hybridizes to influenza virus HA DNA. . Upon BamHI digestion, two bands of 4.6 kb and 1.7 kb that hybridized to the vaccinia HindIII J fragment are produced from the recombinant instead of the single 6 kb fragment produced from wild-type virus. The sizes of these fragments are consistent with the presence of a BamHI site upstream of the TK gene and the introduction of new BamHI sites in the recombinants. In addition, a single 1.7 kb fragment that hybridized to the influenza HA gene is released from vInf1. This represents the entire inserted HA fragment and coincidentally is similar in size to the BamHI fragment that hybridized to vaccinia HindIII J DNA. The orientation of the inserted HA gene is demonstrated by SalI digestion. Cleavage of vInf1 DNA produces a fragment of 6.5 kb that hybridizes to both influenza HA and vaccinia HindIII J DNA probes. This band contains the entire HA gene, except for 90 bp at the, 5' end and nearly 5 kb of vaccinia DNA including sequences downstream of the TK gene. Another 1.3 kb fragment containing sequences upstream of the TK gene hybridizes only to the vaccinia probe.

The above date indicate that vInf1 contains the entire influenza HA gene inserted into the TK gene of vaccinia virus, correctly oriented with respect to the translocated vaccinia promoter. Additionally, the absence of the 5 kb HindIII J fragment indicates that the recombinant is uncontaminated with wild-type virus. The latter conclusion was reached independently by the finding of identic virus titers upon plaque assay in TK⁻ cells in the presence and absence of BUdR.

Example 10.

Figure 2:
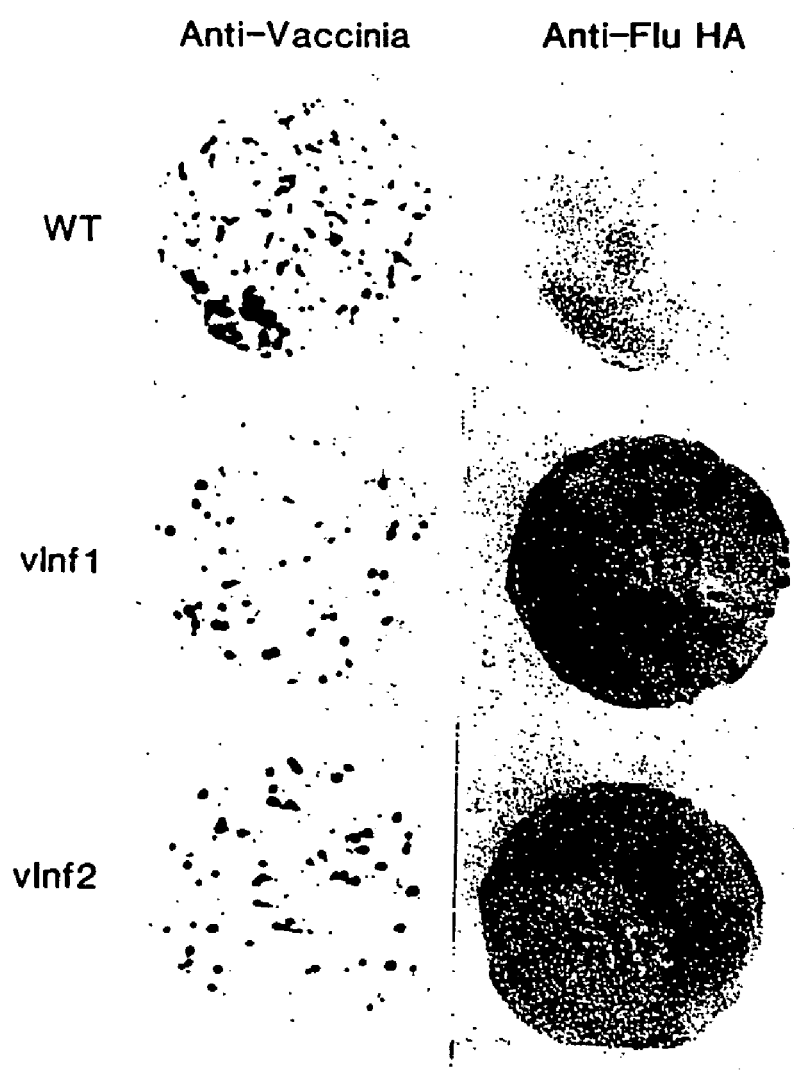
FIG. 2. Expression of influenza HA in cells infected with vInf1 is detected by the binding of antibody prepared against influenza A/Jap, 301/57 to virus plaques.

The expression of influenza HA in cells infected with vInf1 is obtained by the binding of antibody prepared against influenza A/Jap/305/57 to virus plaques. Antibody binding is detected by incubation with $125_I$ staphylococcal A protein followed by autoradiography (FIG. 2). A direct comparison of the stained cell monolayer with the autoradiograph indicates that all vInf1 plaques bound antibody.

Figure 3:
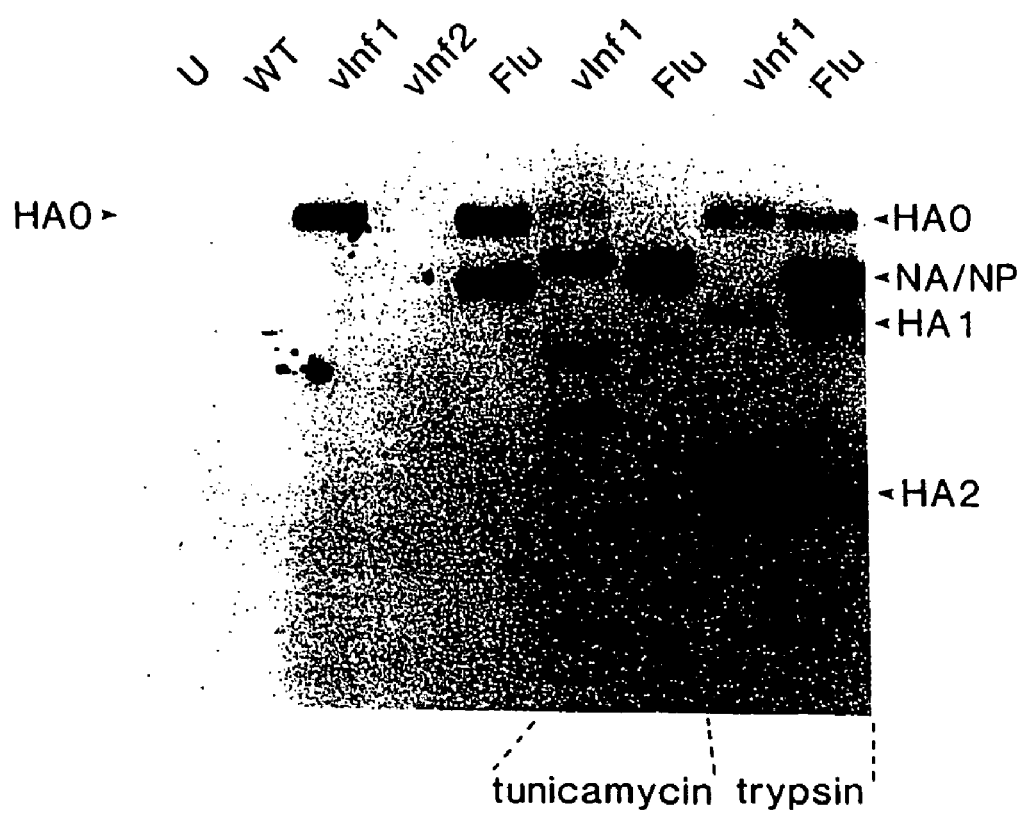
FIG. 3. Immunoprecipitation of pulse-labeled influenza HA polypeptide from cells infected with vInf1.

To characterize the influenza HA polypeptide, cells infected with vaccinia recombinant vInf1 are pulse-labeled with [$^{35}$S]methionine. Cell extracts are then incubated Successively with goat anti-influenza A/Jap/305/57 and fixed staphylococcal cells. Bound polypeptides are dissociated with sodium dodecyl sulfate and resolved by polyacrylamide gel electrophoresis. As seen in the autoradiograph (FIG. 3), a polypeptide of approximately 75,000 daltons (MAC) is specifically immunoprecipitated from cells infected with recombinant vInf1 but not from uninfected cells or those infected with wild-type vaccinia virus. Additionally, this band comigrated with authentic influenza HA immunoprecipitated from cells infected with influenza virus (FIG. 3). Since the antiserum was made against total influenza virus, other polypeptides including the nucleoprotein (NP) and neuraminidase (NA) are also precipitated.

In cell lines permissive for production of infectious influenza virus, the HA is glycosylated, transported to the cell surface and cleaved into two subunits HA1 and HA2. Although the CV-1 cell line used in this invention does not produce significant cleavage of HA into subunits during influenza infection. HA is transported to the surface where it is susceptible to cleavage with exogenous trypsin. Since a significant portion of the influenza HA synthesized in cells infected with recombinant vaccinia virus is cleaved with added trypsin (FIG. 3), it also was transported to the cell surface. Immunofluorescence studies on vInf1 infected cells that were fixed with formaldehyde to prevent cell permeabilization also indicate a surface location of HA.

Tunicamycin, a drug that blocks glycosylation of newly synthesized polypeptides in the rough endoplasmic reticulum by preventing formation of the dolicholigosaccharide donor, is used to investigate whether the HA was glycosylated. This drug reduced the size of the HA polypeptide produced by influenza virus and by the vaccinia recombinant to approximately 63,000 daltons (FIG. 3), consistent with the previously determined size of non-glycosylated HA. These data as well as direct labeling experiments with [$^3$H]glucosamine demonstrate that the HA produced by vInf1 is glycosylated in a manner similar to authentic influenza HA.

Vaccination in animals.

The ability of vaccinia virus recombinants to elicit antibody response to organisms whose DNA was used in preparation of the chimeric gene was first tested in rabbits.

Test I.

Previous studies have shown that HBsAg particles from the blood of human hepatitis B virus carriers are highly, immunogenic and can neutralize the infectivity of hepatitis B virus. Consequently, the question of whether infection of animals with vaccinia virus recombinants that express HBsAg would induce production of anti-HBsAg antibodies was examined.

Rabbits were pre-bled and then infected with either wild-type vaccinia virus or vaccinia wires recombinant vHBs4 by intradermal injection of 10⁸ pfu or virus into 4 sites on the back of each rabbit. Rabbits were bled daily following inoculation and serum was prepared and stored frozen at −70° C. At 5 days, the rabbits developed lesions at the sites of inoculation and by 10 days these lesions were visibly healing. Serum from the rabbits was tested for HBsAg and antibodies against HBsAg by radioimmunoassay, and for vaccinia virus by plaque assay. No HBsAg or vaccinia virus was detectable in the serum. However, by 5 days after inoculation, antibodies against HBsAg were detected (Table 2).

TABLE 2

Production of antibodies against HBsAg
by rabbits vacciniated with recombinant vHBs4

| Days after vaccination | RIA units/0.2 ml of serum | |
|---|---|---|
| | vHBs4 | WT virus |
| 5 | 92 | 8 |
| 6 | 135 | — |
| 7 | 352 | — |
| 8 | >512 | — |
| 9 | >512 | — |
| 10 | >512 | — |
| 11 | 442 | 8 |

Undiluted serum, obtained from rabbits on the days indicted, was tested for antibody to HBsAg by a radioimmunoassay procedure (AUSAB, Abbot Laboratories). An HBsAg positive control human plasma supplied by Abbot Laboratories had a titer of 512 RIA units (see Test 1).

Test II.

The ability of vaccinia virus recombinants to elicit an antibody response to influenza HA was tested in rabbits. The recombinant virus was purified by sucrose gradient centrifugation, and at concentrations 50-fold higher than that used for immunization, contained no detectable influenza HA as judged by the inability to agglutinate chicken red blood cells. Accordingly, synthesis of influenza HA by the recombinant vaccinia virus in inoculated animals is required to stimulate antibody production. Two pairs of rabbits are inoculated intradermally with either wild-type vaccinia virus or vInf1, and sera assayed for anti-bodies to influenza HA by hemagglutination inhibition test on 0, 14, 35 and 62 days after vaccination. In both rabbits vaccinated with vInf1, significant antibody levels were detected by day 14, the titers increasing to 1:128 and 1:64 on day 62. No antibodies to HA were detected in the sera of animals vaccinated with wild-type virus.

To test whether immunization with vaccinia virus recombinants protects animals against influenza virus infection, a hamster model system was used. This experiment tests the efficacy of the vaccine. Groups of ten animals are inoculated with either WT vaccinia, recombinant vInf1 or influenza A/Jap/305/57 and sera taken from each animal on days 0, 12, 22 and 40 is tested for antibodies to influenza HA. As shown in the Table, antibodies to HA were not found in animals vaccinated with wild-type vaccinia virus; however, in all animals inoculated with recombinant vInf1 or influenza A/Jap/305/57, antibodies to influenza HA are detected. Moreover, the mean levels of antibodies in these two groups of animals, are only significantly different on day 40, when the level of antibodies in animals vaccinated with recombinant vInf1 significantly exceed the levels in animals inoculated with influenza virus (Table 3).

The results of challenging all hamsters with influenza virus 40 days after initial inoculation are also shown in the Table. These data show that hamsters

TABLE 3

Antibody responses of hamsters inoculated with WT vaccinia, vaccinia recombinant vInf1 and influenza A/Jap/305/57 and their responses to challenge with influenza A/Jap/305/57

| Animals Inoculated with: | Number of animals tested | Geometric mean HAI antibody titer on indicated days[a] | | | | Number of animals showing >4-fold increase in HAI titer | Response to challenge with influenza A/Jap/305/57 | |
|---|---|---|---|---|---|---|---|---|
| | | 0 | 12 | 22 | 40 | | Number of animals yielding virus | Mean $\log_{10}$ titer ($TCID_{50}$/gm lung day 1) |
| Vaccinia | 10 | ≤2 | ≤2 | ≤2 | ≤2 | 0 | 8 | 4.4 ± 0.6 |
| Recombinant vInf1 | 10 | ≤2 | 74 | 104 | 104 | 10 | 2[c] | 2.6 ± 0.1[e] |
| Influenza A/Jap/305/57 | 10 | ≤2 | 49 | 97 | 49 | 10 | 1[c] | 2.6 ± 0.1[e] |

[a]Antibody titers are reciprocals.
[b]Significantly different, P < 0.05 Fisher's exact test
[c]Virus recovered from these animals was at the lowest level detectable ($10^{3.0}$ $TCID_{50}$/gm lung).
[d]Significantly different, P < 0.01 student's t-test.
[e]For calculation of mean titers, animals from which virus was not recovered were assigned maximum possible values of $10^{2.5}$ $TCID_{50}$/gm lung.

that initially receives wither the vaccinia recombinant vInf1 or influenza virus are resistant to challenge as indicated by a reduction in the number of animals from which virus was recovered and by a decrease in the quantity of virus recovered. Additionally, the resistance of these two groups of animals to influenza infection did not significantly differ.

Test III.

Twenty-week-old golden Syrian hamsters were anesthetized with ether and their lateral abnormal walls were shaved. One side received an intradermal injection of $10^8$ plaque forming units of either wild-type vaccinia or vaccinia recombinant vInf1 in 0.1 ml, and the other side received the same amount of virus by scarification. A separate group of animals received $10^5$ $TCID_{50}$ units of influenza virus A/Jap/305/57 intranasally in 0.1 ml. The three groups of animals (10 per group) were bled via the retrorbital plexus on days 0, 12, 22 and 40 and sera from each animal was tested individually for antibodies to influenza HA by hemagglutination inhibition test using influenza virus A/Jap/305/57 as antigen. On day 40, each hamster was anesthetized by intraperitoneal injection of pentobarbitol and inoculated intranasally with $10^5$ $TCID_{50}$ units of influenza virus A/Jap/305/57 in 0.1 ml. One or two days later, the lungs and nasal turbinates were removed (five animals per day per group) and 10% (w/v) tissue homogenates were prepared and assayed for influenza infectivity on MDCK cell monolayers. As shown in the Table, the influenza virus vaccine is most effective in protecting the hamsters from infection Pairs of female white rabbits, tested as the hamsters were above, were inoculated by intradermal injection of $10^8$ plaque forming units of either wild-type vaccinia or recombinant vInf1 in 0.1 ml. Rabbits were bled from their ears on days 0, 14, 33 and 62 and were tested for antibodies to influenza HA as above. The production of Ab shows that the use of this recombinant is not restricted to one species.

Test IV.

The construction of a recombinant vaccinia virus, designated vHBs4, that expresses the hepatitis B virus surface antigen was described previously (Smith et al., Nature, Vol, 302, p, 490, 1982; patent application Ser. No, 445,892). Three chimpanzees, seronegative for markers of previous hepatitis B virus infection, were intradermally inoculated at a single site on their backs with $10^8$ plaque forming units of vaccinia virus. Two of the chimpanzees received vHBs4 and one received unmodified vaccinia virus as a control. After approximately fourteen weeks, each of the animals were challenged by intravenous administration of $10^{3.5}$ units of hepatitis B virus, strain ayw. For six months thereafter, sera were collected periodically for analysis of hepatitis B virus surface antigen, antibody to the latter, and alanine aminotransferase levels. Hepatitis B virus surface antigen and elevated levels of alanine aminotransferase were found in the serum of the animal inoculated with the unmodified vaccinia virus but not in the animals vaccinated with vHBs4. In contrast, the animals immunized with vBHs4 responded to the hepatitis B virus challenge by producing elevated levels of antibody to the hepatitis B virus surface antigen. These studies clearly showed that a single intradermal vaccination with vHBs4 protected chimpanzees against hepatitis.

Reduced virulence of vaccinia virus recombinants.

For a recombinant vaccinia virus to be used as a vaccine there should be evidence that its virulence is no greater and preferably less than that of unmodified vaccinia virus. To compare virulence, groups of mice were injected intraperitoneally with unmodified vaccinia virus or with recombinant vInf1. At a dose of $10^9$ plaque forming units, 11 out of 12 animals injected with unmodified vaccinia virus died within 7 days, whereas all 6 animals injected with vInf1 survived for at least 21 days. Results similar to the latter also were obtained with mice that received another vaccinia virus recombinant that expresses the herpes simplex 1 virus glycoprotein D gene. Both of the recombinant viruses were constructed in the same manner and are thymidine kinase negative because they have foreign genes inserted into the vaccinia virus thymidine locus. The reduced virulence may be at least partly attributed to the deficiency of thymidine kinase expression since only 1 animal died out of 4 inoculated with a thymidine kinase mutant of the parent virus. These results clearly showed attenuation of the pathogenicity of vaccinia virus caused by insertion of foreign genes into the thymidine kinase locus.

Decreased virulence for primates was shown by intradermal inoculation of chimpanzees with vHBs4. Two chimpanzees that received $10^8$ plaque forming units of vaccinia virus intradermally had small and localized reactions. In contrast, the chimpanzee that received $10^8$ plaque forming units of unmodified vaccinia virus had a much more severe reaction with enlarged necrotic area at the primary site and extension toward the axillary region. Similar evidence for attenuation or reducing the virulence or pathogenicity was also obtained upon intradermal inoculation of rhesus monkeys with a vaccinia virus recombinant containing another foreign gene (malarial plasmodium circumsporozoite gene) inserted into the vaccinia virus thymidine kinase locus.

What is claimed is:

1. A plasmid that comprises (A) a segment comprised of (i) a first DNA sequence encoding a polypeptide that is foreign to poxvirus and (ii) a poxvirus promoter, wherein said promoter is adjacent to and exerts transcriptional control over said first DNA sequence; and, flanking said segment, (B) DNA from a nonessential region of a poxvirus genome.

2. A plasmid according to claim 1, wherein said promoter is from DNA not contained in said nonessential region.

3. A plasmid according to claim 1, wherein said nonessential region is a thymidine kinase gene.

4. A plasmid according to claim 1, wherein said polypeptide is immunogenic.

5. A recombinant poxvirus that comprises a segment comprised of (A) a first DNA sequence encoding a polypeptide that is foreign to poxvirus and (B) a poxvirus promoter, wherein (i) said promoter is adjacent to and exerts transcriptional control over said first DNA sequence and (ii) said segment is positioned within a nonessential genomic region of said recombinant poxvirus.

6. A recombinant poxvirus according to claim 5, wherein said promoter is from DNA not contained in said nonessential region.

7. A recombinant poxvirus according to claim 5, wherein said nonessential region is a thymidine kinase gene.

8. A recombinant poxvirus according to claim 5, wherein said polypeptide is immunogenic.

9. A method for preparing a vector, comprised of the steps of (A) providing a plasmid and (B) incorporating into said plasmid a segment comprising a chimeric gene that contains (i) a first DNA sequence encoding a polypeptide that is foreign to poxvirus; (ii) a poxvirus promoter, wherein said promoter is adjacent to and exerts transcriptional control over said first DNA sequence; and (iii) DNA from a nonessential region of a poxvirus genome, said DNA flanking said chimeric gene such that said plasmid can undergo homologous recombination with a poxvirus genome in a poxvirus-infected cell.

10. A method according to claim 9, further comprising the step of transfecting a poxvirus-infected cell with said plasmid to obtain a recombinant poxvirus wherein said chimeric gene is positioned in a nonessential genomic region thereof.

11. A method for producing a polypeptide, comprising the steps of:
  (A) providing a recombinant poxvirus that contains a segment comprised of (i) a first DNA sequence encoding a polypeptide that is foreign to poxvirus and (ii) a poxvirus promoter, wherein (a) said promoter is adjacent to and exerts transcriptional control over said first DNA sequence and (b) said segment is positioned within a nonessential genomic region of said recombinant poxvirus;
  (B) infecting host cells with said recombinant poxvirus, such that said host cells express said polypeptide; and then
  (C) separating said polypeptide from said host cells.

12. A method according to claim 11, wherein said promoter is from DNA not contained in said nonessential region.

13. A method according to claim 11, wherein said nonessential region is a thymidine kinase gene.

14. A method according to claim 11, wherein said polypeptide is immunogenic.

* * * * *